(12) United States Patent
Wolf et al.

(10) Patent No.: US 11,635,436 B2
(45) Date of Patent: Apr. 25, 2023

(54) COMPOSITIONS AND METHODS FOR ANALYZING CYSTEINE

(71) Applicant: Georgetown University, Washington, DC (US)

(72) Inventors: Christian Wolf, Arlington, VA (US); Fathima Yushra Thanzeel, Washington, DC (US)

(73) Assignee: GEORGETOWN UNIVERSITY, Washington, DC (US)

(*) Notice: Subject to any disclaimer, the term of this patent is extended or adjusted under 35 U.S.C. 154(b) by 83 days.

(21) Appl. No.: 16/608,147

(22) PCT Filed: Apr. 24, 2018

(86) PCT No.: PCT/US2018/029109
§ 371 (c)(1),
(2) Date: Oct. 24, 2019

(87) PCT Pub. No.: WO2018/200498
PCT Pub. Date: Nov. 1, 2018

(65) Prior Publication Data
US 2020/0150128 A1    May 14, 2020

Related U.S. Application Data

(60) Provisional application No. 62/489,411, filed on Apr. 24, 2017.

(51) Int. Cl.
*G01N 33/68* (2006.01)
*G01N 21/33* (2006.01)
(Continued)

(52) U.S. Cl.
CPC ......... *G01N 33/6815* (2013.01); *G01N 21/33* (2013.01); *G01N 21/64* (2013.01);
(Continued)

(58) Field of Classification Search
CPC .... G01N 33/6815; G01N 21/33; G01N 21/64; G01N 33/52; G01N 2800/00;
(Continued)

(56) References Cited

U.S. PATENT DOCUMENTS

| 2015/0010938 A1 | 1/2015 | Strongin et al. |
| 2016/0039792 A1 | 2/2016 | Bogyo et al. |
| 2016/0195532 A1 | 7/2016 | Carroll et al. |

FOREIGN PATENT DOCUMENTS

CN          104610960 A        5/2015

OTHER PUBLICATIONS

Zhang, Caishun, et al. "Thiol-activated triplet-triplet annihilation upconversion: study of the different quenching effect of electron acceptor on the singlet and triplet excited states of bodipy." The Journal of organic chemistry 80.11 (2015): 5674-5686. (Year: 2015).*

(Continued)

*Primary Examiner* — Jennifer Wecker
*Assistant Examiner* — Oyeleye Alexander Alabi
(74) *Attorney, Agent, or Firm* — Troutman Pepper Hamilton Sanders LLP (Rochester)

(57) ABSTRACT

The present invention relates to compositions and methods for determining the absolute configuration of D/L-cysteine and/or the enantiomeric composition of cysteine and/or the concentration of total cysteine in a sample. Uses of the composition and method are also described.

11 Claims, 24 Drawing Sheets

(51) Int. Cl.
   *G01N 21/64*      (2006.01)
   *G01N 33/52*      (2006.01)
   *C07C 309/65*     (2006.01)
   *C07C 309/73*     (2006.01)

(52) U.S. Cl.
   CPC ........... *G01N 33/52* (2013.01); *C07C 309/65* (2013.01); *C07C 309/73* (2013.01)

(58) Field of Classification Search
   CPC .............. G01N 33/6812; C07C 309/65; C07C 309/73; C07D 277/66
   See application file for complete search history.

(56) References Cited

OTHER PUBLICATIONS

Ramachandran et al. ("2, 4-Dinitro-1-naphthyl 4-toluenesulfonate." Acta Crystallographica Section E: Structure Reports Online 64.5 (2008): o873-o873) (Year: 2008).*
PCT/US2018/029109, International Preliminary Reporton Patentability (dated Nov. 7, 2019).
PCT/US2018/029109, International Search Report and Written Opinion (dated Aug. 1, 2018).
PubChem. CID No. 10008, https://pubchem.ncbi.nlm.nih.gov/compound/10008 (retrieved Jun. 8, 2018).

* cited by examiner

COMPOSITIONS AND METHODS FOR ANALYZING CYSTEINE

This application is a national stage application under 35 U.S.C. § 371 of PCT International Application No. PCT/US2018/029109, filed Apr. 24, 2018, which claims the priority benefit of U.S. Provisional Patent Application Ser. No. 62/489,411, filed Apr. 24, 2017, which is hereby incorporated by reference in its entirety.

This invention was made with government support under grant numbers CHE-1213019 and CHE-1464547 awarded by the National Science Foundation. The government has certain rights in this invention.

FIELD OF THE INVENTION

The present technology relates to probes and methods for evaluating the absolute configuration, and/or enantiomeric composition, and/or overall concentration of free cysteine in a sample.

BACKGROUND OF THE INVENTION

Amino acids are inarguably among the most predominant and important chiral compounds in nature. For a long time, it has been assumed that L-amino acids are almost exclusively present in higher animals while the corresponding D-enantiomers would only be utilized by microorganisms and bacteria. In recent years, this view of homochirality has been revisited as substantial amounts of D-amino acids have been detected in mammals and humans. In fact, D- and L-amino acids are not mutually exclusive and often co-exist as nonracemic mixtures. This is the case in mammalian and human tissue where they occur in the free form or in proteins as well as in the central nervous system (CNS). (Hamase et al., *J. Chromatogr. B* 781:73-91 (2002); Walsh, *ACS Chem. Biol.* 9:1653-1661 (2014).) The total amount and enantiomeric excess or ratio (ee or er) of amino acids in the CNS play an important role in human physiology and pathology and they have been associated with neurological disorders such as schizophrenia, Parkinson's, Huntington's, and Alzheimer's disease and other neurodegenerative or psychiatric disorders such as traumatic stress and anxiety attacks. (Fuchs et al., *Mol. Genet. Metab.* 85:168-180 (2005).) The widespread occurrence, racemization processes, and pivotal biological functions of D-amino acids have important implications in the life sciences. (Friedman, *Chem. Biodivers.* 7:1491-1530 (2010); D-AMINO ACIDS IN CHEMISTRY, LIFE SCIENCES, AND BIOTECHNOLOGY (Hans Bruckner & Noriko Fujii eds., 2011); Friedman & Levin, *Amino Acids* 42:1553-1582 (2012); Simon et al., *J. Am. Chem. Soc.* 138: 12099-12111 (2016).) The ability to quantify both concentration and enantiomeric composition of amino acids with artificial receptors is considered very promising for the study, diagnosis, and treatment of diseases and ageing. (Turner, *Chem. Soc. Rev.* 42:3184-3196 (2013).) Although increasing efforts have recently been directed to optical chemosensing, a robust method that accurately reports the total amount and ee/er at the micromolar concentration level of a specific amino acid in the presence of others is still elusive. (Leung et al., *Chem. Soc. Rev.* 41:448-479 (2012); Wolf & Bentley, *Chem. Soc. Rev.* 42:5408-5424 (2013); Wu et al., *Chem. Rev.* 115:7893-7943 (2015); Zhou & Yoon, *Chem. Soc. Rev.* 41:52-67 (2012).)

The change in the dogmatic perception of mammalian amino acid homochirality has shifted increasing attention to the natural occurrence and the distinct biological, nutritional, and medicinal roles of the D-enantiomer of cysteine and of D/L-enantiomeric mixtures in recent years. (Sit et al., *Acc. Chem. Res.* 44: 261-268 (2011); Kimura, *Nitric Oxide* 41:4-10 (2014); Yuan & Liang, *Org. Biomol. Chem.* 12:865-871 (2014); Shibuya et al., *Nat. Commun.* 4:1366 (2013).) These findings underscore the need for a means that permits fast determination of the absolute configuration, enantiomeric composition (ee and/or er), and overall concentration of cysteine in aqueous mixtures. Selective stereochemical cysteine analysis, however, is particularly complicated because of the common presence of chemically similar biothiols. In addition to other amino acids, homocysteine (Hcy) and glutathione (GSH) typically interfere with molecular recognition processes and further complicate both substrate-specific detection and enantioselective quantification. Significant progress with regard to chemosensing of biothiols with molecular UV or fluorescent probes has been reported over the past decade. (Chen et al., *Chem. Soc. Rev.* 39:2120-2135 (2010); Lee et al., *Chem. Soc. Rev.* 44:4185-4191 (2015); Kubota & Hamachi, *Chem. Soc. Rev.* 44: 4454-4471 (2015); Kowada et al., *Chem. Soc. Rev.* 44:4953-4972 (2015); Niu et al., *Chem. Soc. Rev.* 44:6143-6160 (2015).) A variety of fluorescence, colorimetric/UV, and electrochemical assays for selective quantification of Cys, Hcy, or GSH have been introduced. (Maeda et al., *Angew. Chem. Int. Ed.* 44:2922-2925 (2005); Bouffard et al., *Org. Lett.* 10:37-40 (2008); Zhang et al., *Org. Lett.* 11:1257-1260 (2009); Lin et al., *Chem. Eur. J* 15:5096-5103 (2009); Li et al., *Chem. Commun.* 5904-5906 (2009); Liu et al., *J. Am. Chem. Soc.* 136:574-577 (2014); Wang et al., *Chem. Commun.* 52:827-830 (2016); Shen et al., *Anal. Methods* 8:2420-2426 (2016); Tang et al., *RSC Adv.* 6:34996-35000 (2016).) (For selective thiophenol sensing, see Jiang et al., *Angew. Chem. Int. Ed.* 46:8445-8448 (2007); Han & Kim, *Tetrahedron* 60:11251-11257 (2004); Huo et al., *Org. Lett.* 11:4918-4921 (2009); Dai et al., *Anal. Chim. Acta* 900:103-110 (2015); and Luo et al., *Angew. Chem. Int. Ed.* 54:14053-14056 (2015).) While some of these methods can be used for quantitative analysis of cysteine in aqueous solutions in the presence of Hcy and GSH, additional information about the enantiomeric composition cannot be obtained. The use of silver nanoparticles for the detection of cysteine enantiomers has shown promise but does not achieve combined concentration and ee analysis. (Zhang & Ye, *Anal. Chem.* 83:1504-1509 (2011).)

Therefore, there is still a need for a practical chiroptical sensing assay that is compatible with low cysteine concentrations (e.g., micromolar) and allows rapid determination of the absolute configuration, enantiomeric composition, and overall concentration of free-form cysteine.

The present technology is directed to overcoming these and other deficiencies in the art.

SUMMARY OF THE INVENTION

One aspect of the present technology relates to a compound comprising a chromophore of the formula

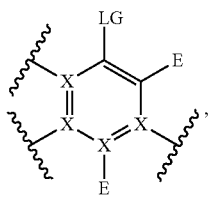

wherein:
each X is independently C or N;
each E is independently hydrogen or an electron withdrawing group selected from the group consisting of —CF$_3$, —C(O)—R$_a$, —SO$_2$—R$_a$, —CN, and —NO$_2$, with the proviso that at least one E is an electron withdrawing group; and
LG is a leaving group.

In at least one embodiment of this aspect of the present technology, the compound is a compound of Formula I:

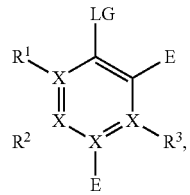

I wherein:
each X is independently C or N;
each E is independently hydrogen or an electron withdrawing group selected from the group consisting of —CF$_3$, —C(O)—R$_a$, —SO$_2$—R$_a$, —CN, and —NO$_2$, with the proviso that at least one E is an electron withdrawing group;
LG is a leaving group;
R$^1$ and R$^2$ are each independently absent or selected from the group consisting of —R$_a$, -cycloalkyl, -heterocycloalkyl, -aryl, and -heteroaryl; or R$_1$ and R$_2$, together with the carbon atoms to which they are attached, form a cycloalkyl, heterocycloalkyl, aryl, or heteroaryl;
R$^3$ is absent or selected from the group consisting of —R$_a$, -cycloalkyl, -heterocycloalkyl, -aryl, and -heteroaryl; and
each R$_a$ is independently selected from the group consisting of —H, -alkyl, —O-alkyl, —N-alkyl, -alkenyl, —O-alkenyl, —N-alkenyl, -alkynyl, —O-alkynyl, —N-alkynyl, -aryl, —O-aryl, —N-aryl, -heteroaryl, —O-heteroaryl, —N-heteroaryl, -cycloalkyl, —O-cycloalkyl, —N-cycloalkyl, -heterocycloalkyl, —O— heterocycloalkyl, and —N-heterocycloalkyl.

Another aspect of the present technology relates to an analytical method comprising:
contacting a sample potentially containing D-cysteine, L-cysteine, or a mixture thereof with a probe according to the present technology, wherein said contacting is carried out under conditions effective to result in double ipso-substitution of any cysteine present in the sample; and
determining, based on any double ipso-substituted cysteine that forms, the absolute configuration of D/L-cysteine in the sample, and/or the enantiomeric composition of cysteine in the sample, and/or the total concentration of cysteine in the sample.

Described herein are probes that carry a transferable aryl/heteroaryl moiety for substrate-specific optical analysis of cysteine. These probes provide smooth N,S-di(hetero)arylation of cysteine via double ipso-substitution and concomitant (chir)optical (e.g., UV and circular dichroism) sensor readouts at high wavelengths. The absolute configuration of the major cysteine enantiomer and the enantiomeric composition (i.e., enantiomeric excess and/or enantiomeric ratio) of D/L-cysteine can be determined from the sign and amplitude, respectively, of the induced CD signals, and a new UV absorption band correlates to the overall cysteine concentration. The methods described herein use a practical mix-and-measure protocol and fast UV (or other colorimetric) and CD (or other optical) measurements that provide accurate stereochemical information with samples covering a wide concentration range and drastically different D/L-cysteine ratios in, e.g., body fluids. The presence of other amino acids and biothiols does not interfere with the cysteine sensing.

BRIEF DESCRIPTION OF THE DRAWINGS

FIG. 1A shows the structures of probes 1-3 (top) and a general scheme (bottom) of double ipso-substitution for chiroptical cysteine sensing using probe 1 as an example. FIG. 1B is CD spectra showing circular dichroism responses to the D and L enantiomers of cysteine using probe 1 (left) and probe 3 (right). The CD measurements were taken at 0.11 mM in acetonitrile:water (4:1).

FIG. 2A is the UV (left) and CD (right) spectra of Cys samples of varying concentration and ee using two equivalents of probe 1. FIG. 2B shows the NMR analysis of the formation of diarylated cysteine 4. All NMR spectra were collected using deuterated acetonitrile:water (4:1) as solvent and K$_2$CO$_3$ as base. (1) Reference spectrum of diarylated cysteine 4. (2) Potassium phenolate. (3) Cysteine sensing experiment after 7 minutes. (4) Probe 1. (5) Cysteine. FIG. 2C is the CD spectra of CD sensing of L-cysteine using probe 1 and different base additives showing the effect of the base on the CD response. (At 425 nm, the lines correspond, from top to bottom, to LiOH, Na$_2$CO$_3$, CsOH, NaOH, DBU, TBAOH, K$_2$CO$_3$, and KOH.) The CD and UV measurements were taken in acetonitrile:water (4:1) at 50 and 30 μM, respectively.

FIG. 3A shows the structures of the amino acids and biothiols tested. FIG. 3B is the CD (left) and UV (right) spectra showing sensing of L-Cys using probe 1 in the presence of the L-enantiomers of Phe, Ala, Ser, and Tyr. FIG. 3C is the CD (left) and UV (right) spectra showing substrate specificity of probe 1 in the presence of homocysteine (HCy) and glutathione (GSH). The CD and UV measurements were taken in acetonitrile:water (4:1) at 110 and 30 μM, respectively.

FIG. 4A is the CD spectra (left) showing the CD response of probe 1 to L-cysteine at varying concentrations and a plot (right) of the CD amplitudes at 376 nm (positive Y-axis) and 423 nm (negative Y-axis) of the sensing adduct versus cysteine concentration. The peak amplitudes are proportional to the cysteine concentrations tested, which shows the linearity of ee sensing vs L-Cys sample concentration. FIG. 4B is the CD spectra (left) showing quantitative chiroptical sensing of L-cysteine and D-cysteine at 15 μM concentration and a plot (right) showing the linear relationship between the CD effects at 377 nm (lower left and upper right quadrants) and 417 nm (upper left and lower right quadrants) versus enantiomeric excess (% ee) of cysteine. (See FIG. 34 for the CD spectra of each ee tested.)

FIG. 24A is the UV spectra showing the UV analysis of the reaction between cysteine and probe 1 at different time points. FIG. 24B is a plot of the absorbance of probe 1 at 355 nm versus time.

DETAILED DESCRIPTION

Figure 1A:
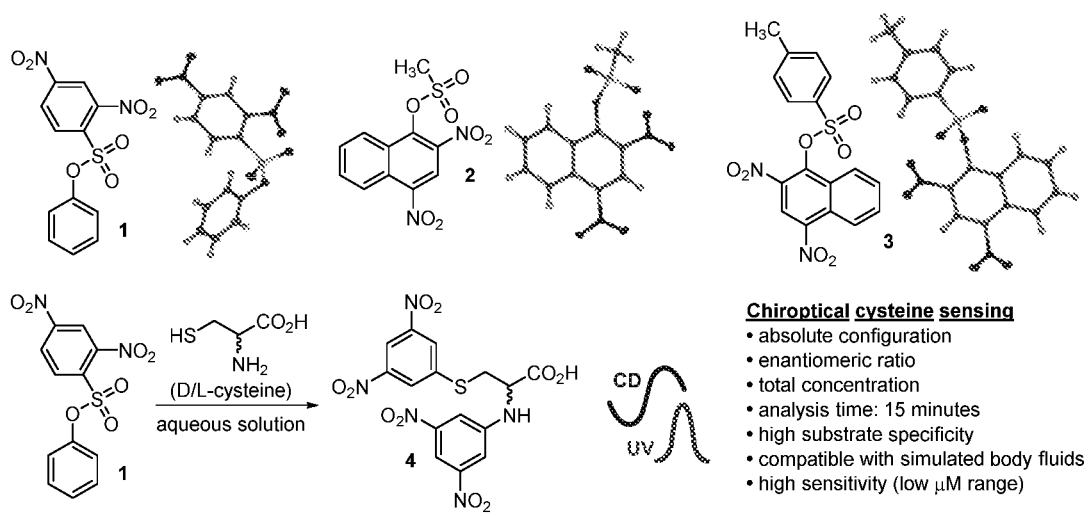
FIGS. 1A-B relate to chiroptical cysteine sensing.

The present technology relates to compositions and methods related to a practical chiroptical sensing assay that is compatible with aqueous solutions (e.g., body fluids) and allows rapid determination of the absolute configuration, enantiomeric composition, and overall concentration of cysteine at low (e.g., micromolar) concentrations. The methods are highly specific for free-form cysteine, even in the presence of agents that interfere with known molecular recognition processes, such as other amino acids and biothiols (e.g., homocysteine and glutathione).

One aspect of the present technology relates to a compound comprising a chromophore of the formula

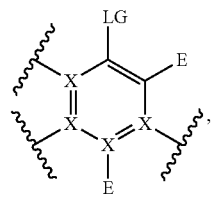

wherein:
each X is independently C or N;
each E is independently hydrogen or an electron withdrawing group selected from the group consisting of —$CF_3$, —C(O)—$R_a$, —$SO_2$—$R_a$, —CN, and —$NO_2$, with the proviso that at least one E is an electron withdrawing group; and LG is a leaving group.

In at least one embodiment, the compound is a compound of Formula I:

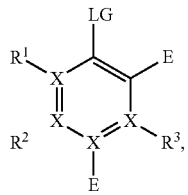

I wherein:

each X is independently C or N;

each E is independently hydrogen or an electron withdrawing group selected from the group consisting of —$CF_3$, —C(O)—$R_a$, —$SO_2$—$R_a$, —CN, and —$NO_2$, with the proviso that at least one E is an electron withdrawing group;

LG is a leaving group;

$R^1$ and $R^2$ are each independently absent or selected from the group consisting of —$R_a$, -cycloalkyl, -heterocycloalkyl, -aryl, and -heteroaryl; or $R_1$ and $R_2$, together with the carbon atoms to which they are attached, form a cycloalkyl, heterocycloalkyl, aryl, or heteroaryl;

$R^3$ is absent or selected from the group consisting of —$R_a$, -cycloalkyl, -heterocycloalkyl, -aryl, and -heteroaryl; and each $R_a$ is independently selected from the group consisting of —H, -alkyl, —O-alkyl, —N-alkyl, -alkenyl, —O-alkenyl, —N-alkenyl, -alkynyl, —O-alkynyl, —N-alkynyl, -aryl, —O-aryl, —N-aryl, -heteroaryl, —O-heteroaryl, —N-heteroaryl, -cycloalkyl, —O-cycloalkyl, —N-cycloalkyl, -heterocycloalkyl, —O— heterocycloalkyl, and —N-heterocycloalkyl.

As used herein, the term "alkyl" refers to a straight or branched, saturated aliphatic radical containing one to about twenty (e.g., 1, 2, 3, 4, 5, 6, 7, 8, 9, 10, 11, 12, 13, 14, 15, 16, 17, 18, 19, 20, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 2-3, 2-4, 2-5, 2-6, 2-7, 2-8, 2-9, 2-10, 2-11, 2-12, 2-13, 2-14, 2-15, 2-16, 2-17, 2-18, 2-19, 2-20, 3-4, 3-5, 3-6, 3-7, 3-8, 3-9, 3-10, 3-11, 3-12, 3-13, 3-14, 3-15, 3-16, 3-17, 3-18, 3-19, 3-20, 4-5, 4-6, 4-7, 4-8, 4-9, 4-10, 4-11, 4-12, 4-13, 4-14, 4-15, 4-16, 4-17, 4-18, 4-19, 4-20, 5-6, 5-7, 5-8, 5-9, 5-10, 5-11, 5-12, 5-13, 5-14, 5-15, 5-16, 5-17, 5-18, 5-19, 5-20, 6-7, 6-8, 6-9, 6-10, 6-11, 6-12, 6-13, 6-14, 6-15, 6-16, 6-17, 6-18, 6-19, 6-20, 7-8, 7-9, 7-10, 7-11, 7-12, 7-13, 7-14, 7-15, 7-16, 7-17, 7-18, 7-19, 7-20, 8-9, 8-10, 8-11, 8-12, 8-13, 8-14, 8-15, 8-16, 8-17, 8-18, 8-19, 8-20, 9-10, 9-11, 9-12, 9-13, 9-14, 9-15, 9-16, 9-17, 9-18, 9-19, 9-20, 10-11, 10-12, 10-13, 10-14, 10-15, 10-16, 10-17, 10-18, 10-19, 10-20, 11-12, 11-13, 11-14, 11-15, 11-16, 11-17, 11-18, 11-19, 11-20, 12-13, 12-14, 12-15, 12-16, 12-17, 12-18, 12-19, 12-20, 13-14, 13-15, 13-16, 13-17, 13-18, 13-19, 13-20, 14-15, 14-16, 14-17, 14-18, 14-19, 14-20, 15-16, 15-17, 15-18, 15-19, 15-20, 16-17, 16-18, 16-19, 16-20, 17-18, 17-19, 17-20, 18-19, 18-20, 19-20) carbon atoms and, unless otherwise indicated, may be optionally substituted. In at least one embodiment, the alkyl is a $C_1$-$C_{10}$ alkyl. In at least one embodiment, the alkyl is a $C_1$-$C_6$ alkyl. Suitable examples include, without limitation, methyl, ethyl, propyl, isopropyl, butyl, sec-butyl, isobutyl, tert-butyl, 3-pentyl, and the like.

As used herein, the term "alkenyl" refers to a straight or branched aliphatic unsaturated hydrocarbon of formula $C_nH_{2n}$ having from two to about twenty (e.g., 2, 3, 4, 5, 6, 7, 8, 9, 10, 11, 12, 13, 14, 15, 16, 17, 18, 19, 20, 2-3, 2-4, 2-5, 2-6, 2-7, 2-8, 2-9, 2-10, 2-11, 2-12, 2-13, 2-14, 2-15, 2-16, 2-17, 2-18, 2-19, 2-20, 3-4, 3-5, 3-6, 3-7, 3-8, 3-9, 3-10, 3-11, 3-12, 3-13, 3-14, 3-15, 3-16, 3-17, 3-18, 3-19, 3-20, 4-5, 4-6, 4-7, 4-8, 4-9, 4-10, 4-11, 4-12, 4-13, 4-14, 4-15, 4-16, 4-17, 4-18, 4-19, 4-20, 5-6, 5-7, 5-8, 5-9, 5-10, 5-11, 5-12, 5-13, 5-14, 5-15, 5-16, 5-17, 5-18, 5-19, 5-20, 6-7, 6-8, 6-9, 6-10, 6-11, 6-12, 6-13, 6-14, 6-15, 6-16, 6-17, 6-18, 6-19, 6-20, 7-8, 7-9, 7-10, 7-11, 7-12, 7-13, 7-14, 7-15, 7-16, 7-17, 7-18, 7-19, 7-20, 8-9, 8-10, 8-11, 8-12, 8-13, 8-14, 8-15, 8-16, 8-17, 8-18, 8-19, 8-20, 9-10, 9-11, 9-12, 9-13, 9-14, 9-15, 9-16, 9-17, 9-18, 9-19, 9-20, 10-11, 10-12, 10-13, 10-14, 10-15, 10-16, 10-17, 10-18, 10-19, 10-20, 11-12, 11-13, 11-14, 11-15, 11-16, 11-17, 11-18, 11-19, 11-20, 12-13, 12-14, 12-15, 12-16, 12-17, 12-18, 12-19, 12-20, 13-14, 13-15, 13-16, 13-17, 13-18, 13-19, 13-20, 14-15, 14-16, 14-17, 14-18, 14-19, 14-20, 15-16, 15-17, 15-18, 15-19, 15-20, 16-17, 16-18, 16-19, 16-20, 17-18, 17-19, 17-20, 18-19, 18-20, 19-20) carbon atoms in the chain and, unless otherwise indicated, may be optionally substituted. Exemplary alkenyls include, without limitation, ethylenyl, propylenyl, n-butylenyl, and i-butylenyl.

As used herein, the term "alkynyl" refers to a straight or branched aliphatic unsaturated hydrocarbon of formula $C_nH_{2n-2}$ having from two to about twenty (e.g., 2, 3, 4, 5, 6, 7, 8, 9, 10, 11, 12, 13, 14, 15, 16, 17, 18, 19, 20, 2-3, 2-4, 2-5, 2-6, 2-7, 2-8, 2-9, 2-10, 2-11, 2-12, 2-13, 2-14, 2-15, 2-16, 2-17, 2-18, 2-19, 2-20, 3-4, 3-5, 3-6, 3-7, 3-8, 3-9, 3-10, 3-11, 3-12, 3-13, 3-14, 3-15, 3-16, 3-17, 3-18, 3-19, 3-20, 4-5, 4-6, 4-7, 4-8, 4-9, 4-10, 4-11, 4-12, 4-13, 4-14, 4-15, 4-16, 4-17, 4-18, 4-19, 4-20, 5-6, 5-7, 5-8, 5-9, 5-10, 5-11, 5-12, 5-13, 5-14, 5-15, 5-16, 5-17, 5-18, 5-19, 5-20, 6-7, 6-8, 6-9, 6-10, 6-11, 6-12, 6-13, 6-14, 6-15, 6-16, 6-17, 6-18, 6-19, 6-20, 7-8, 7-9, 7-10, 7-11, 7-12, 7-13, 7-14, 7-15, 7-16, 7-17, 7-18, 7-19, 7-20, 8-9, 8-10, 8-11, 8-12, 8-13, 8-14, 8-15, 8-16, 8-17, 8-18, 8-19, 8-20, 9-10, 9-11, 9-12, 9-13, 9-14, 9-15, 9-16, 9-17, 9-18, 9-19, 9-20, 10-11, 10-12, 10-13, 10-14, 10-15, 10-16, 10-17, 10-18, 10-19, 10-20, 11-12, 11-13, 11-14, 11-15, 11-16, 11-17, 11-18, 11-19, 11-20, 12-13, 12-14, 12-15, 12-16, 12-17, 12-18, 12-19, 12-20, 13-14, 13-15, 13-16, 13-17, 13-18, 13-19, 13-20, 14-15, 14-16, 14-17, 14-18, 14-19, 14-20, 15-16, 15-17, 15-18, 15-19, 15-20, 16-17, 16-18, 16-19, 16-20, 17-18, 17-19, 17-20, 18-19, 18-20, 19-20) carbon atoms in the chain and, unless otherwise indicated, may be optionally substituted. Exemplary alkynyls include acetylenyl, propynyl, butynyl, 2-butynyl, 3-methylbutynyl, and pentynyl.

As used herein, the terms "perfluoroalkyl", "perfluoroalkenyl", and "perfluoroalkynyl" refer to an alkyl, alkenyl, or alkynyl group as defined above in which the hydrogen atoms on at least one of the carbon atoms have all been replaced with fluorine atoms.

As used herein, the term "cycloalkyl" refers to a non-aromatic saturated or unsaturated monocyclic or polycyclic ring system which may contain 3 to 24 (3, 4, 5, 6, 7, 8, 9, 10, 11, 12, 13, 14, 15, 16, 17, 18, 19, 20, 21, 22, 23, 24, 3-4, 3-5, 3-6, 3-7, 3-8, 3-9, 3-10, 3-11, 3-12, 3-13, 3-14, 3-15, 3-16, 3-17, 3-18, 3-19, 3-20, 3-21, 3-22, 3-23, 3-24, 4-5, 4-6, 4-7, 4-8, 4-9, 4-10, 4-11, 4-12, 4-13, 4-14, 4-15, 4-16, 4-17, 4-18, 4-19, 4-20, 4-21, 4-22, 4-23, 4-24, 5-6, 5-7, 5-8, 5-9, 5-10, 5-11, 5-12, 5-13, 5-14, 5-15, 5-16, 5-17, 5-18, 5-19, 5-20, 5-21, 5-22, 5-23, 5-24, 6-7, 6-8, 6-9, 6-10, 6-11, 6-12, 6-13, 6-14, 6-15, 6-16, 6-17, 6-18, 6-19, 6-20, 6-21, 6-22, 6-23, 6-24, 7-8, 7-9, 7-10, 7-11, 7-12, 7-13, 7-14, 7-15, 7-16, 7-17, 7-18, 7-19, 7-20, 7-21, 7-22, 7-23, 7-24, 8-9, 8-10, 8-11, 8-12, 8-13, 8-14, 8-15, 8-16, 8-17, 8-18, 8-19, 8-20, 8-21, 8-22, 8-23, 8-24, 9-10, 9-11, 9-12, 9-13, 9-14, 9-15, 9-16, 9-17, 9-18, 9-19, 9-20, 9-21, 9-22, 9-23, 9-24, 10-11, 10-12, 10-13, 10-14, 10-15, 10-16, 10-17, 10-18, 10-19, 10-20, 10-21, 10-22, 10-23, 10-24, 11-12, 11-13, 11-14, 11-15, 11-16, 11-17, 11-18, 11-19, 11-20, 11-21, 11-22, 11-23, 11-24, 12-13, 12-14, 12-15, 12-16, 12-17, 12-18, 12-19, 12-20, 12-21, 12-22, 12-23, 12-24, 13-14, 13-15, 13-16, 13-17, 13-18, 13-19, 13-20, 13-21, 13-22, 13-23, 13-24, 14-15, 14-16, 14-17, 14-18, 14-19, 14-20, 14-21, 14-22, 14-23, 14-24, 15-16, 15-17, 15-18, 15-19, 15-20, 15-21, 15-22, 15-23, 15-24, 16-17, 16-18, 16-19, 16-20, 16-21, 16-22, 16-23, 16-24, 17-18, 17-19, 17-20, 17-21, 17-22, 17-23, 17-24, 18-19, 18-20, 18-21, 18-22, 18-23, 18-24, 19-20, 19-21, 19-22, 19-23, 19-24, 20-21, 20-22, 20-23, 20-24, 21-22, 22-23, 22-24, 23-24) carbon atoms, which may include at least one double bond and, unless otherwise indicated, the ring system may be optionally substituted. Exemplary cycloalkyl groups include, without limitation, cyclopropyl, cyclobutyl, cyclopentyl, cyclohexyl, cyclopropenyl, cyclobutenyl, cyclopentenyl, cyclohexenyl, anti-bicyclopropane, and syn-bicyclopropane.

As used herein, the term "heterocycloalkyl" refers to a cycloalkyl group as defined above having at least one O, S, and/or N interrupting the carbocyclic ring structure. Examples of heterocycloalkyls include, without limitation, piperidine, piperazine, morpholine, thiomorpholine, pyrrolidine, tetrahydrofuran, pyran, tetrahydropyran, and oxetane. Unless otherwise indicated, the heterocycloalkyl ring system may be optionally substituted.

As used herein, the term "aryl" refers to an aromatic monocyclic or polycyclic ring system from 6 to 24 (6, 7, 8, 9, 10, 11, 12, 13, 14, 15, 16, 17, 18, 19, 20, 21, 22, 23, 24, 6-7, 6-8, 6-9, 6-10, 6-11, 6-12, 6-13, 6-14, 6-15, 6-16, 6-17, 6-18, 6-19, 6-20, 6-21, 6-22, 6-23, 6-24, 7-8, 7-9, 7-10, 7-11, 7-12, 7-13, 7-14, 7-15, 7-16, 7-17, 7-18, 7-19, 7-20, 7-21, 7-22, 7-23, 7-24, 8-9, 8-10, 8-11, 8-12, 8-13, 8-14, 8-15, 8-16, 8-17, 8-18, 8-19, 8-20, 8-21, 8-22, 8-23, 8-24, 9-10, 9-11, 9-12, 9-13, 9-14, 9-15, 9-16, 9-17, 9-18, 9-19, 9-20, 9-21, 9-22, 9-23, 9-24, 10-11, 10-12, 10-13, 10-14, 10-15, 10-16, 10-17, 10-18, 10-19, 10-20, 10-21, 10-22, 10-23, 10-24, 11-12, 11-13, 11-14, 11-15, 11-16, 11-17, 11-18, 11-19, 11-20, 11-21, 11-22, 11-23, 11-24, 12-13, 12-14, 12-15, 12-16, 12-17, 12-18, 12-19, 12-20, 12-21, 12-22, 12-23, 12-24, 13-14, 13-15, 13-16, 13-17, 13-18, 13-19, 13-20, 13-21, 13-22, 13-23, 13-24, 14-15, 14-16, 14-17, 14-18, 14-19, 14-20, 14-21, 14-22, 14-23, 14-24, 15-16, 15-17, 15-18, 15-19, 15-20, 15-21, 15-22, 15-23, 15-24, 16-17, 16-18, 16-19, 16-20, 16-21, 16-22, 16-23, 16-24, 17-18, 17-19, 17-20, 17-21, 17-22, 17-23, 17-24, 18-19, 18-20, 18-21, 18-22, 18-23, 18-24, 19-20, 19-21, 19-22, 19-23, 19-24, 20-21, 20-22, 20-23, 20-24, 21-22, 22-23, 22-24, 23-24) carbon atoms and, unless otherwise indicated, the ring system may be optionally substituted. Aryl groups of the present technology include, but are not limited to, groups such as phenyl, naphthyl, azulenyl, phenanthrenyl, anthracenyl, fluorenyl, pyrenyl, triphenylenyl, chrysenyl, naphthacenyl, biphenyl, triphenyl, and tetraphenyl. In at least one embodiment, an aryl within the context of the present technology is a 6 or 10 membered ring. In at least one embodiment, each aryl is phenyl or naphthyl.

As used herein, the term "heteroaryl" refers to an aryl group as defined above having at least one O, S, and/or N interrupting the carbocyclic ring structure. Examples of heteroaryl groups include, without limitation, pyrrolyl, pyrazolyl, imidazolyl, triazolyl, furyl, thiophenyl, oxazolyl, isoxazolyl, thiazolyl, isothiazolyl, oxadiazolyl, thiadiazolyl, pyridyl, pyrazinyl, pyrimidinyl, pyridazinyl, triazinyl, thienopyrrolyl, furopyrrolyl, indolyl, azaindolyl, isoindolyl, indolinyl, indolizinyl, indazolyl, benzimidazolyl, imidazopyridinyl, benzotriazolyl, benzoxazolyl, benzoxadiazolyl, benzothiazolyl, pyrazolopyridinyl, triazolopyridinyl, thienopyridinyl, benzothiadiazolyl, benzofuyl, benzothiophenyl, quinolinyl, isoquinolinyl, tetrahydroquinolyl, tetrahydroisoquinolyl, cinnolinyl, quinazolinyl, quinolizilinyl, phthalazinyl, benzotriazinyl, chromenyl, naphthyridinyl, acrydinyl, phenanzinyl, phenothiazinyl, phenoxazinyl, pteridinyl, and purinyl. Additional heteroaryls are described in COMPREHENSIVE HETEROCYCLIC CHEMISTRY: THE STRUCTURE, REACTIONS, SYNTHESIS AND USE OF HETEROCYCLIC COMPOUNDS (Katritzky et al. eds., 1984), which is hereby incorporated by reference in its entirety. Unless otherwise indicated, the heteroaryl ring system may be optionally substituted.

The term "monocyclic" as used herein indicates a molecular structure having one ring.

The term "polycyclic" as used herein indicates a molecular structure having two or more rings, including, but not limited to, fused, bridged, spiro, or covalently bound rings. In at least one embodiment, the polycyclic ring system is a bicyclic, tricyclic, or tetracyclic ring system. In at least one embodiment, the polycyclic ring system is fused. In at least one embodiment, the polycyclic ring system is a bicyclic ring system such as naphthyl or biphenyl.

As used herein, the term "optionally substituted" indicates that a group may have a substituent at each substitutable atom of the group (including more than one substituent on a single atom), provided that the designated atom's normal valency is not exceeded and the identity of each substituent is independent of the others. Up to three H atoms in each residue are replaced with alkyl, halogen, haloalkyl, hydroxy, alkoxy (especially $C_1$-$C_3$), carboxy, ester, amide, carbonate, carbamate, urea, cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy. "Unsubstituted" atoms bear all of the hydrogen atoms dictated by their valency. When a substituent is keto (i.e., =O), then two hydrogens on the atom are replaced. Combinations of substituents and/or variables are permissible only if such combinations result in stable compounds; by "stable compound" is meant a compound that is sufficiently robust to survive isolation to a useful degree of purity from a reaction mixture, and formulation into an efficacious agent.

As used herein, the term "halogen" includes fluorine, bromine, chlorine, and iodine while the term "halide" includes fluoride, bromide, chloride, and iodide anion.

In at least one embodiment of the compounds of the present technology, each X is C. In other embodiments, one or more X moieties are N. One, two, three, or four of the X moieties may be N. For example, when one X moiety is N, a pyridine ring is provided in the compound, and when two X moieties are N, a pyridazine, pyrimidine, or pyrazine ring is provided in the compound. In a particularly preferred embodiment of the present technology, each X is C, providing a phenyl ring.

In at least one embodiment of the compounds of the present technology, each E is independently an electron withdrawing group. Suitable electron withdrawing groups include —$CF_3$, —C(O)—$R_a$, —$SO_2$—$R_a$, —CN, and —$NO_2$, where each $R_a$ is independently selected from the group consisting of —H, -alkyl, —O-alkyl, —N— alkyl, -alkenyl, —O-alkenyl, —N-alkenyl, -alkynyl, —O-alkynyl, —N-alkynyl, -aryl, —O-aryl, —N-aryl, -heteroaryl, —O-heteroaryl, —N-heteroaryl, -cycloalkyl, —O— cycloalkyl, —N-cycloalkyl, -heterocycloalkyl, —O-heterocycloalkyl, and —N— heterocycloalkyl. In a particularly preferred embodiment, each E is —NO$_2$.

LG in the compounds of the present technology is a leaving group. Suitable leaving groups are substituents that are present on the compound that can be displaced (preferably for nucleophilic aromatic substitution). Suitable leaving groups are apparent to a skilled artisan. In at least one embodiment, the leaving group is selected from the group consisting of halogen (e.g., —I, —Br, —Cl, —F), —OR$_b$, —OC(O)R$_b$, —OS(O)$_2$R$_b$, —S(O)$_2$—O—R$_b$, —N$_2^+$, —N$^+$(R$_b$)$_3$, —S$^+$(R$_b$)$_2$, and —P$^+$(R$_b$)$_3$; where each R$_b$ is independently selected from the group consisting of hydrogen, -alkyl, —O— alkyl, —N-alkyl, -alkenyl, —O-alkenyl, —N-alkenyl, -alkynyl, —O-alkynyl, —N— alkynyl, -perfluoroalkyl, -perfluoroalkenyl, -perfluoroalkynyl, -aryl, —O-aryl, —N-aryl, -heteroaryl, —O-heteroaryl, —N-heteroaryl, -cycloalkyl, —O-cycloalkyl, —N— cycloalkyl, -heterocycloalkyl, —O-heterocycloalkyl, and —N-heterocycloalkyl. In at least one embodiment, the leaving group is

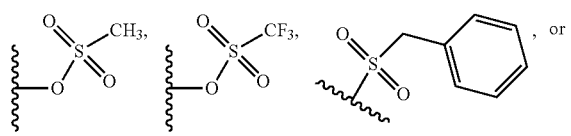

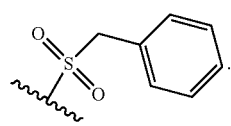

In a preferred embodiment, the leaving group is

In certain embodiments, R$^1$ and R$^2$ in the compound of Formula I are each independently absent or selected from the group consisting of —R$_a$, -cycloalkyl, -heterocycloalkyl, -aryl, and -heteroaryl. In other embodiments, R$_1$ and R$_2$, together with the carbon atoms to which they are attached, form a cycloalkyl, heterocycloalkyl, aryl, or heteroaryl. In at least one embodiment, R$_1$ and R$_2$, together with the carbon atoms to which they are attached, form a naphthalene, benzimidazole, quinoline, or indole ring. In a preferred embodiment, R$_1$ and R$_2$, together with the carbon atoms to which they are attached, form a naphthalene ring.

In at least one embodiment, R$^1$, R$^2$, and R$^3$ of the compound of Formula I are each hydrogen.

In at least one embodiment, the compound is selected from the group consisting of

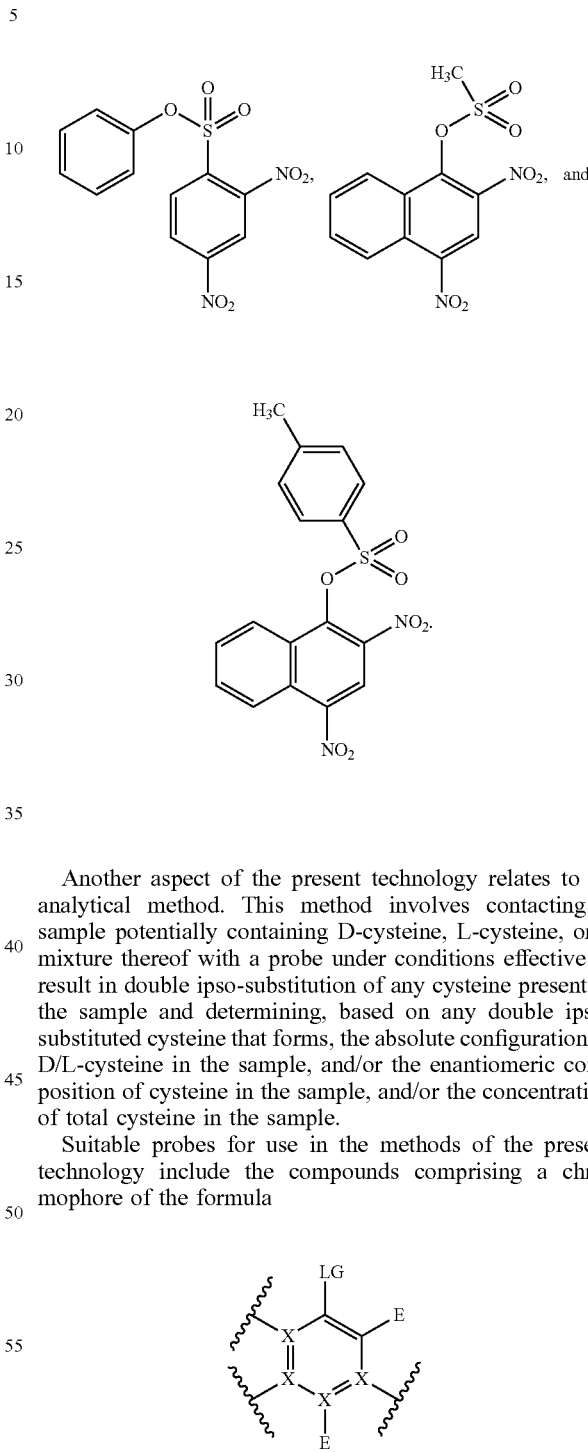

Another aspect of the present technology relates to an analytical method. This method involves contacting a sample potentially containing D-cysteine, L-cysteine, or a mixture thereof with a probe under conditions effective to result in double ipso-substitution of any cysteine present in the sample and determining, based on any double ipso-substituted cysteine that forms, the absolute configuration of D/L-cysteine in the sample, and/or the enantiomeric composition of cysteine in the sample, and/or the concentration of total cysteine in the sample.

Suitable probes for use in the methods of the present technology include the compounds comprising a chromophore of the formula

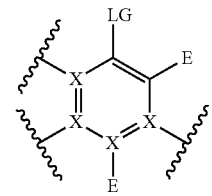

(including compounds of Formula I and all embodiments thereof) described herein.

As used herein, "double ipso-substitution," or "double ipso-substituted" refers to the disubstitution reaction between free-form cysteine and probe of the present technology. By way of example, the following scheme presents a general overview of a double ipso-substitution reaction.

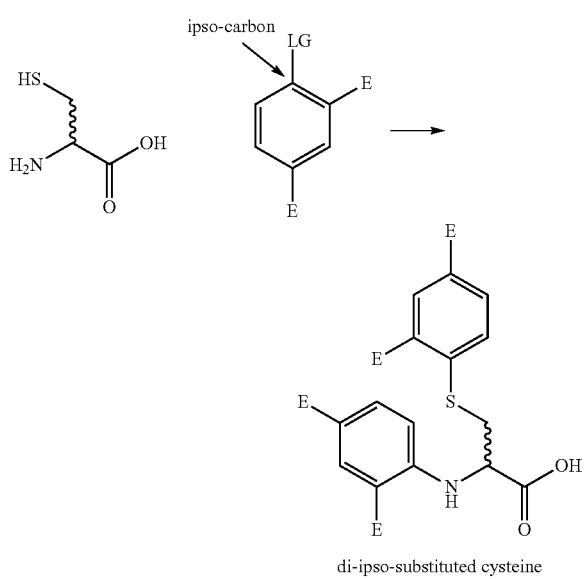

di-ipso-substituted cysteine

As used herein, the term "absolute configuration" of D/L-cysteine refers to the identification of the major cysteine enantiomer present in a sample. The absolute configuration of D/L-cysteine can be assigned from the chiroptical signal of the double ipso-substituted cysteine complexes that form. This assignment can be based on the sense of chirality induction with a reference or by analogy. The absolute configuration of the major cysteine enantiomer is indicated by the sign of the produced Cotton effect. The chiroptical signal of the complexes can be measured using standard techniques, which will be apparent to the skilled artisan. Such techniques include circular dichroism spectroscopy (e.g., STEREOCHEMISTRY OF ORGANIC COMPOUNDS 1003-07 (E. L. Eliel & S. H. Wilen eds., 1994); DYNAMIC STEREOCHEMISTRY OF CHIRAL COMPOUNDS 140-43 (Christian Wolf ed., 2008), each of which is hereby incorporated by reference in its entirety), optical rotatory dispersion (e.g., STEREOCHEMISTRY OF ORGANIC COMPOUNDS 999-1003 (E. L. Eliel & S. H. Wilen eds., 1994), which is hereby incorporated by reference in its entirety), and polarimetry (e.g., STEREOCHEMISTRY OF ORGANIC COMPOUNDS 217-21, 1071-80 (E. L. Eliel & S. H. Wilen eds., 1994); DYNAMIC STEREOCHEMISTRY OF CHIRAL COMPOUNDS 140-43 (Christian Wolf ed., 2008), each of which is hereby incorporated by reference in its entirety). As will be apparent to the skilled artisan, absolute configuration can be determined by reference to a standard. By way of example, a standard could be the optical spectra (or information regarding the sign of the Cotton effect at relevant wavelengths produced thereby) obtained from standard samples generated by mixing enantiomerically pure samples of each enantiomer of cysteine with a probe (i.e., the particular probe to be used with the test sample or a probe that would produce substantially the same results). The chiroptical signal of the test sample can be measured by generating an optical spectrum of the double ipso-substituted cysteine in the test sample under analogous conditions. The absolute configuration of the major cysteine enantiomer originally present in the test sample can then be determined by comparing the optical spectrum of the test sample to that of the standard sample(s). As will be apparent to the skilled artisan, different probes, reaction conditions (solvent, etc.), and detection methods (circular dichroism, optical rotatory dispersion, or polarimetry) may produce different Cotton effects with regard to the amplitude, shape, sign, and relevant wavelengths. Those skilled in the art will know how to adjust these factors so that the test conditions sufficiently match the conditions used to generate the standard.

As used herein, determining the "enantiomeric composition" of a sample refers to determining: (1) the enantiomeric excess of D-cysteine, (2) the enantiomeric excess of L-cysteine, (3) the enantiomeric excess of both D-cysteine and L-cysteine, (4) the enantiomeric ratio of D:L cysteine, (5) the enantiomeric ratio of L:D cysteine, or (5) any combination thereof. The term "enantiomeric ratio" (er) is the ratio of the percentage of one cysteine enantiomer in a mixture to that of the other enantiomer. The term "enantiomeric excess" (ee) is the difference between the percentage of one cysteine enantiomer and the percentage of the other cysteine enantiomer. For example, a sample which contains 75% L-cysteine and 25% D-cysteine will have an enantiomeric excess of 50% of L-cysteine and an enantiomeric ratio (D:L) of 25:75. The enantiomeric excess/ratio can be determined by correlating the chiroptical signal of the double ipso-substituted cysteine complexes that form to the enantiomeric excess/ratio of the analyte(s). The enantiomeric composition is based on the induced amplitude of chiroptical signal. The chiroptical signal can be measured using standard techniques, which will be apparent to the skilled artisan. Such techniques include circular dichroism spectroscopy (e.g., STEREOCHEMISTRY OF ORGANIC COMPOUNDS 1003-07 (E. L. Eliel & S. H. Wilen eds., 1994); DYNAMIC STEREOCHEMISTRY OF CHIRAL COMPOUNDS 140-43 (Christian Wolf ed., 2008), each of which is hereby incorporated by reference in its entirety), optical rotatory dispersion (e.g., STEREOCHEMISTRY OF ORGANIC COMPOUNDS 999-1003 (E. L. Eliel & S. H. Wilen eds., 1994), which is hereby incorporated by reference in its entirety), and polarimetry (e.g., STEREOCHEMISTRY OF ORGANIC COMPOUNDS 217-21, 1071-80 (E. L. Eliel & S. H. Wilen eds., 1994); DYNAMIC STEREOCHEMISTRY OF CHIRAL COMPOUNDS 140-43 (Christian Wolf ed., 2008), each of which is hereby incorporated by reference in its entirety). As will be apparent to the skilled artisan, enantiomeric composition can be determined by reference to a standard. By way of example, a standard could be the optical spectra (or information regarding the induced amplitude of the signal at relevant wavelengths produced thereby) obtained from standard samples generated by mixing enantiomerically pure samples of each enantiomer of cysteine with a probe (i.e., the particular probe to be used with the test sample or a probe that would produce substantially the same results). The chiroptical signal of the test sample can be measured by generating an optical spectrum of the double ipso-substituted cysteine in the test sample under analogous conditions. The enantiomeric composition of the cysteine originally present in the sample can then be determined by comparing the optical spectrum of the test sample to that of the standard sample(s) and performing the appropriate mathematical calculation(s) to determine the ee/er of the enantiomer(s) of interest. As noted above, different probes, reaction conditions (solvent, etc.), and detection methods (circular dichroism, optical rotatory dispersion, or polarimetry) may produce different Cotton effects with regard to the amplitude, shape, sign, and relevant wavelengths. Those skilled in the art will know how to adjust these factors so that the test conditions sufficiently match the conditions used to generate the standard.

The total concentration of cysteine (i.e., D- plus L-) can be determined by correlating a non-chiroptical spectroscopic signal of the double ipso-substituted cysteine complexes that form to the concentration of total cysteine. The non-chiroptical spectroscopic signal can be measured using standard techniques, which will be apparent to the skilled artisan. Such techniques include, but are not limited to, UV (including UV/Vis) spectroscopy (PRINCIPLES OF INSTRUMENTAL ANALYSIS 342-47 (Douglas A. Skoog et al. eds., $5^{th}$ ed. 1998), which is hereby incorporated by reference in its entirety), fluorescence spectroscopy, and other spectroscopic techniques. By way of example, a standard could be the spectroscopic spectra (e.g., UV, fluorescence) (or relevant information about the spectra) obtained from standard samples generated by mixing serial titrations of cysteine with a probe (i.e., the particular probe to be used with the test sample or a probe that would produce substantially the same results). The spectroscopic signal (e.g., UV, fluorescence) of the double ipso-substituted cysteine can be measured by generating a spectrum (e.g., UV, fluorescence) of the test sample under analogous conditions. The total concentration of the cysteine originally present in the sample can then be determined by comparing the spectrum of the test sample to the titration curve of the standard samples (or relevant values obtained from the titration curve). As will be apparent to the skilled artisan, if the enantiomeric ratio of cysteine is also determined, the concentration of individual enantiomers originally present in the test sample can be determined by comparing the enantiomeric excess to the total cysteine concentration.

In at least one embodiment of the present technology, the absolute configuration of D/L-cysteine in the sample is determined. In another embodiment, the enantiomeric composition of cysteine in the sample is determined. In another embodiment, the concentration of total cysteine in the sample is determined.

In at least one preferred embodiment of the present technology, more than one of the absolution configuration, enantiomeric composition, and total cysteine concentration are determined. For example, the analytical method of the present technology may be used to determine the absolute configuration of D/L-cysteine in the sample and the concentration of total cysteine in the sample. Alternatively, the analytical method of the present technology may be used to determine the enantiomeric composition of cysteine in the sample and the concentration of total cysteine in the sample. In a preferred embodiment, the analytical method of the present technology is used to determine the absolute configuration of D/L-cysteine in the sample, the enantiomeric composition of cysteine in the sample, and the concentration of total cysteine in the sample. In a particularly preferred embodiment, the absolute configuration of D/L-cysteine in the sample, the enantiomeric composition of cysteine in the sample, and the concentration of total cysteine in the sample are all determined concomitantly (i.e., by obtaining a chiroptical signal (e.g., CD) and a non-chiroptical spectroscopic signal (e.g., UV) simultaneously or substantially simultaneously).

The methods of the present technology can be used to determine the absolute configuration, enantiomeric composition, and/or total cysteine concentration in a sample even when the cysteine is present at low concentrations. In at least one embodiment, the analytical method of the present technology is carried out on a sample in which the cysteine is present in micromolar concentrations. The analytical methods of the present technology may also be carried out on samples in which the cysteine concentration is above or below the micromolar range. In at least one embodiment, the sample contains cysteine in the nanomolar range and the absolute configuration of D/L cysteine in the sample, the total concentration of cysteine in the sample, or both are determined.

The analytical methods of the present technology can be used to determine the characteristics (absolute configuration, enantiomeric composition, and/or total cysteine concentration) of free-form cysteine in a sample. The analytical methods of the present technology can selectively detect free-form cysteine even in samples containing other biological agents, such as proteins (including proteins containing cysteine), other free-form amino acids, and other biological thiols such as L-homocysteine and L-glutathione.

Suitable samples include any aqueous or non-aqueous solution that potentially contains D-cysteine, L-cysteine, or a mixture thereof. In a preferred embodiment, the sample is an aqueous solution. The solution may be biological or non-biological. As will be apparent to the skilled artisan, an otherwise solid sample can be suspended in, mixed with, etc., a liquid vehicle to produce a suitable aqueous or non-aqueous solution and then tested.

In at least one embodiment, the sample is a biological sample from an animal. Suitable biological samples include, without limitation, blood, plasma, brain extracellular fluid, cerebrospinal fluid, tissue, cells, cell extracts, cell lysates, serum, semen, amniotic fluid, sputum, urine, feces, bodily fluids, bodily secretions, bodily excretions, circulating tumor cells, tumor, tumor biopsy, and exosomes. In at least one preferred embodiment, the sample is brain extracellular fluid or cerebrospinal fluid.

Suitable animals include, for example, vertebrates, e.g., mammals, fish, reptiles, birds, and amphibians. Suitable mammals include, for example, primates, felines, canines, equines, camelids, bovines, caprines, ovines, swine, rabbits, and rodents. For example, the methods of the present technology can be used to analyze cysteine in a sample from a human subject, a laboratory animal (e.g., monkeys, chimpanzees, rabbits, rats, mice, guinea pigs, hamsters, zebrafish, frogs), or a veterinary animal, such as livestock (e.g., cattle, sheep, pigs, goats, horses, camels, llamas, alpacas, rodents) and pets (e.g., cats, dogs). In a preferred embodiment, the animal is a human subject.

As will be apparent to the skilled artisan, the present methods are especially suitable for evaluating cysteine wherever cysteine plays an important biological function in its free form. For example, in at least one preferred embodiment, the sample is a biological sample of a patient (human or other animal) having or suspected of having or at risk of having a disorder mediated by free form cysteine.

By way of example, free form cysteine plays an important biological function in the brain and has been implicated in neurodegenerative diseases. In at least one embodiment, the sample is a biological sample of a patient having or suspected of having or at risk of having a neurodegenerative disease. Without being bound by any particular theory, it is envisioned that the present technology has utility in identifying and/or detecting and/or monitoring the pathology of a neurodegenerative disease in a human subject by detecting the absolute configuration of D/L-cysteine, and/or the enantiomeric composition of cysteine, and/or the concentration of total cysteine in a neurological sample, such as brain extracellular fluid or cerebrospinal fluid. Examples of neurodegenerative diseases include, but are not limited to, amyotrophic lateral sclerosis (ALS), frontotemporal lobar degeneration (FTLD), Parkinson's disease, Huntington's disease, mild cognitive impairment (MCI), Alzheimer's disease, and diseases associated with TPD-43 proteinopathy.

Free form cysteine has also been implicated in metabolic syndrome (including, without limitation, central adiposity, hyperglycemia, hypertension, dyslipidemia, and insulin resistance), diabetes (e.g., Type 2 diabetes), obstructive sleep apnea, irritable bowel disease/inflammatory bowel disease, and diseases associated with skeletal wasting or muscle fatigue (e.g., HIV/SIV infection, cancer, major injuries, sepsis, Crohn's disease, ulcerative colitis, and chronic fatigue syndrome). (See Mohorco et al., *BioMedRes. Int.* Article ID 418681 (2015); Cintra et al., *Chest* 139(2):246-52 (2011); Dröge et al., *FASEB J.* 11(13):1077-89 (1997); Hack et al., *FASEB J.* 11(1):84-92 (1997); Jain, *European J. Clin. Nutr.* 68:1148-53 (2014); Sido et al., *Gut* 42(4): 485-92 (1998), each of which is hereby incorporated by reference in its entirety.) In at least one embodiment, the sample is a biological sample of a patient having or suspected of having or at risk of having any of these disorders. Without being bound by any particular theory, it is envisioned that the present technology has utility in identifying and/or detecting and/or monitoring the pathology of any of these disorders in a subject by detecting the absolute configuration of D/L-cysteine, and/or the enantiomeric composition of cysteine, and/or the concentration of total cysteine in a relevant biological sample (especially blood, plasma, or serum).

The analytical method may further comprise the steps of providing the sample and providing the probe. Suitable ways of obtaining test samples will be readily apparent to the skilled artisan. As will also be apparent to the skilled artisan, probes may be made using (or adapting as needed), the synthesis strategies described in the Examples.

The present technology may be further illustrated by reference to the following examples.

EXAMPLES

The following examples are provided to illustrate embodiments of the present technology, but they are by no means intended to limit its scope.

Example 1—General Materials and Methods

Synthesis.

Probes 1, 2, and 3 described herein were synthesized using literature procedures. All reagents and solvents were commercially available and used without further purification. Reactions were carried out under inert conditions and the products were purified by flash chromatography on silica gel. The structures of the isolated compounds were identified by spectroscopic analyses and the purity was confirmed by elemental analysis. Further details are described in Example 2.

Crystallographic Analysis.

Single crystals of 1, 2 and 3 were obtained by slow evaporation of solutions in acetonitrile or chloroform. Single crystal X-ray analysis was performed at 296 K using a Siemens platform diffractometer with graphite monochromated Mo-Kα radiation ($\lambda=0.71073$ Å). Data were integrated and corrected using the Apex 2 program. The structures were solved by direct methods and refined with full-matrix least-square analysis using SHELX-97-2 software. Non-hydrogen atoms were refined with anisotropic displacement parameter. More details and crystallographic data can be found in Example 3.

Spectroscopic Analysis.

$^1$H-NMR and $^{13}$C-NMR spectra, including DEPT and 2D NMR measurements, were obtained at 400 MHz and 100 MHz, respectively, using deuterated acetone, chloroform, or acetonitrile/water mixtures as solvents. Chemical shifts were reported in ppm relative to TMS or the solvent peak. CD spectra were collected with a standard sensitivity of 100 mdeg, a data pitch of 0.5 nm, a bandwidth of 1 nm, in a continuous scanning mode with a scanning speed of 500 nm/min and a response of 1 s, using a quartz cuvette (1 cm path length). The data were baseline corrected and smoothed using a binomial equation. UV spectra were collected with an average scanning time of 0.0125 s, a data interval of 5.00 nm, and a scan rate of 400 nm/s. Full range NMR spectra, CD spectra, and UV spectra together with detailed information on sample preparation are provided in the subsequent Examples.

Example 2-Synthesis and Characterization of Cysteine Probes and N,S-Bis(2,4-Dinitrophenyl)Cysteine Synthesis of phenyl 2,4-dinitrobenzenesulfonate (1)

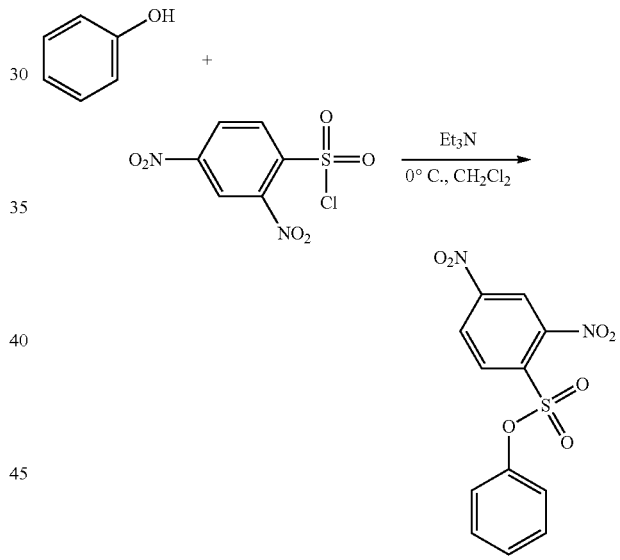

Figure 5A:
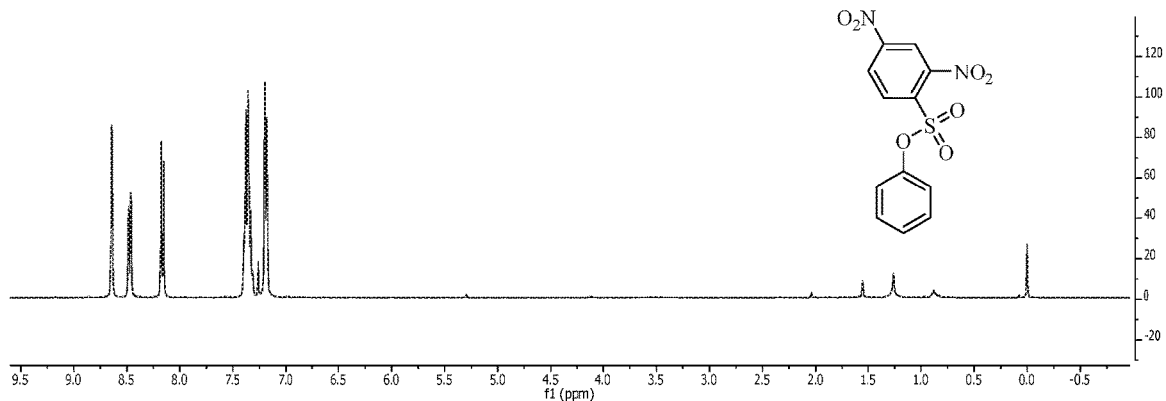
FIGS. 5A-B are the $^1$H NMR (FIG. 5A) and $^{13}$C NMR (FIG. 5B) spectra of probe 1 in CDCl$_3$.
Figure 5B:
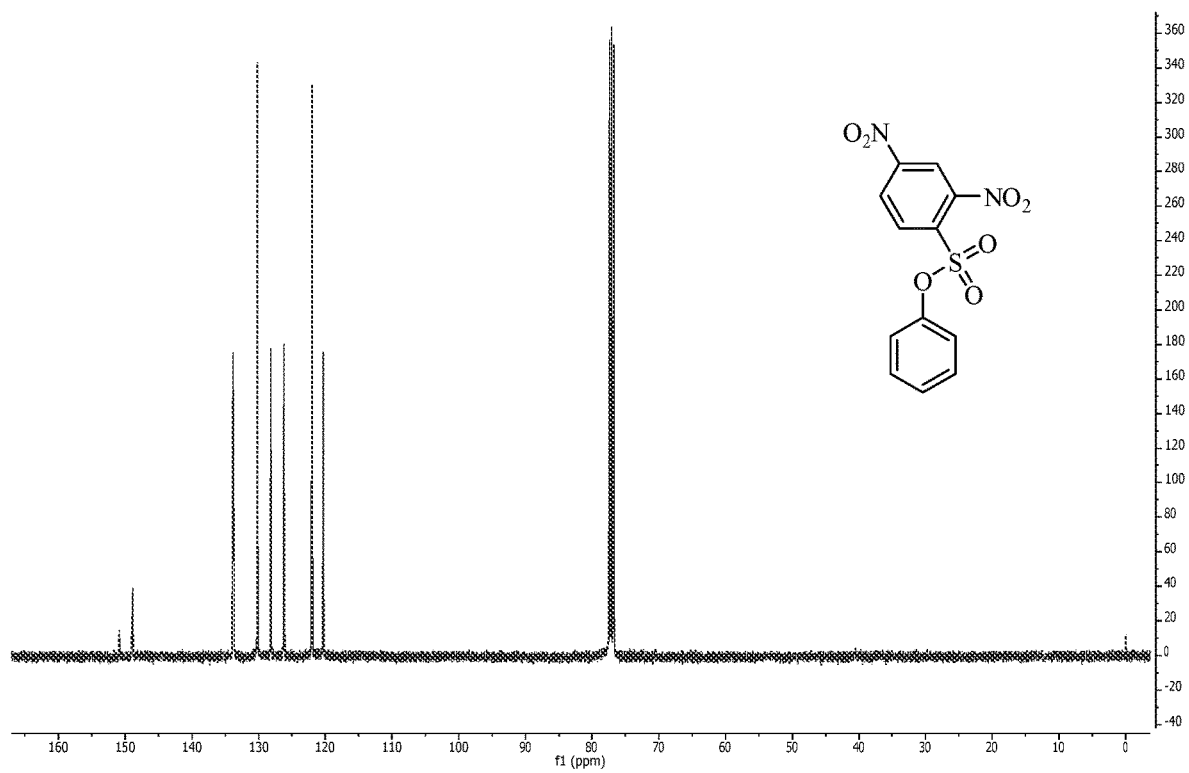

A mixture of phenol (282.3 mg, 3.0 mmol) and triethylamine (460 μL, 3.3 mmol) was stirred in anhydrous $CH_2Cl_2$ (2 mL) for 1 hour at 0° C. Then, 2,4-dinitrosulfonyl chloride (1.32 g, 4.95 mmol) in $CH_2Cl_2$ (3 mL) was added dropwise to the reaction mixture. After stirring for 18 hours, the reaction was quenched with water and extracted with $CH_2Cl_2$. The combined organic layers were dried over $MgSO_4$ and concentrated in vacuo. Purification by flash chromatography on silica gel (10% EtOAc in hexanes) afforded 833.5 mg (2.57 mmol, 86% yield) of a light yellow solid. $^1$H NMR (400 MHz, $CDCl_3$): δ=8.65 (d, J=2.2 Hz, 1H), 8.48 (dd, J=8.6 Hz, 2.1 Hz, 1H), 8.17 (d, J=8.6 Hz, 1H), 7.44-7.30 (m, 3H), 7.20 (d, J=7.9 Hz, 2H). $^{13}$C NMR (100 MHz, $CDCl_3$): δ=120.4, 122.1, 126.41, 128.4, 130.4, 133.8, 134.0, 149.0, 151.0. Anal. Calcd. for $C_{12}H_8N_2O_7S$: C, 44.45; H, 2.49; N, 8.64. Found: C, 44.59; H, 2.58; N, 8.51. See FIGS. 5A-B.

Synthesis of 2,4-dinitronaphthalen-1-yl methanesulfonate (2)

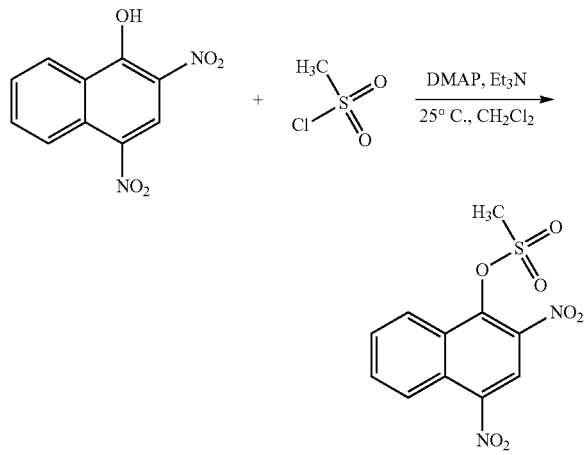

Figure 6A:
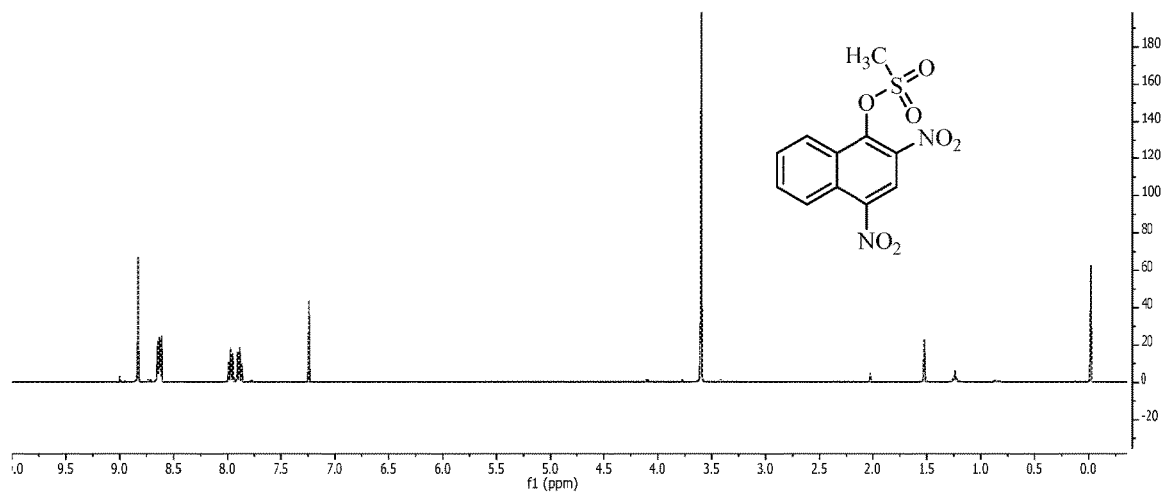
FIGS. 6A-B are the $^1$H NMR (FIG. 6A) and $^{13}$C NMR (FIG. 6B) spectra of probe 2 in CDCl$_3$.
Figure 6B:
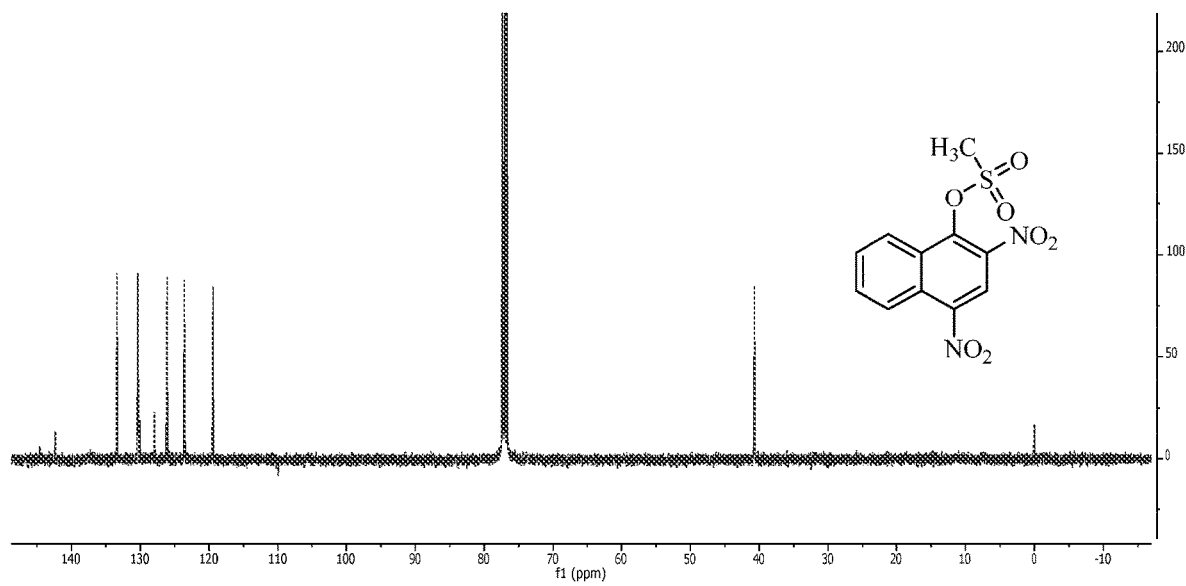

Methanesulfonyl chloride (46.0 µL, 0.593 mmol) was added dropwise to a solution of a 2,4-dinitronaphth-1-ol (123.9 mg, 0.539 mmol), triethylamine (82.7 µL, 0.593 mmol), and DMAP (6.6 mg, 0.054 mmol) in $CH_2Cl_2$ (2 mL) at room temperature. After the reaction was complete, the mixture was washed with water and extracted with $CH_2Cl_2$. The combined organic layers were dried over $MgSO_4$ and concentrated in vacuo. Purification by flash column chromatography on silica gel (20% EtOAc in hexanes) afforded 84.0 mg (0.27 mmol, 54%) of a yellow solid. $^1$H NMR (400 MHz, $CDCl_3$): δ=8.85 (s, 1H), 8.67-8.58 (m, 2H), 7.99 (ddd, J=8.7, 7.0, 1.3 Hz, 1H), 7.91 (ddd, J=8.1, 7.0, 1.1 Hz, 1H), 3.62 (s, 3H). $^{13}$C NMR (100 MHz, $CDCl_3$): δ=40.7, 119.4, 123.6, 126.1, 128.0, 130.0, 130.3, 133.4, 142.3. Anal. Calcd. for $C_{11}H_8N_2O_7S$: C, 42.31; H, 2.58; N, 8.97. Found: C, 42.41; H, 2.70; N, 8.85. See FIGS. 6A-B.

Synthesis of 2,4-dinitronaphthalen-1-yl 4-toluenesulfonate (3)

Figure 7A:
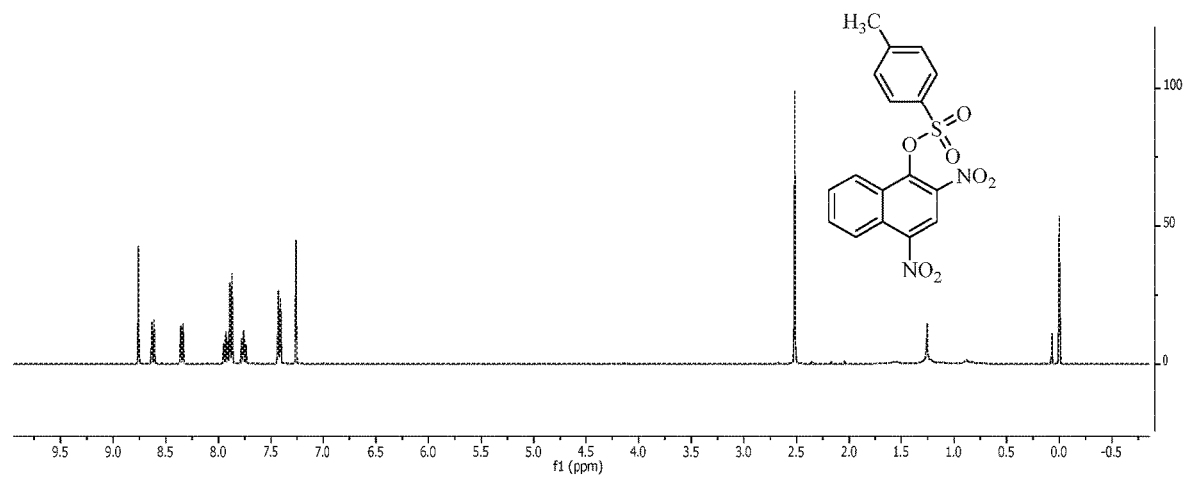
FIGS. 7A-B are the $^1$H NMR (FIG. 7A) and $^{13}$C NMR (FIG. 7B) spectra of probe 3 in CDCl$_3$.
Figure 7B:
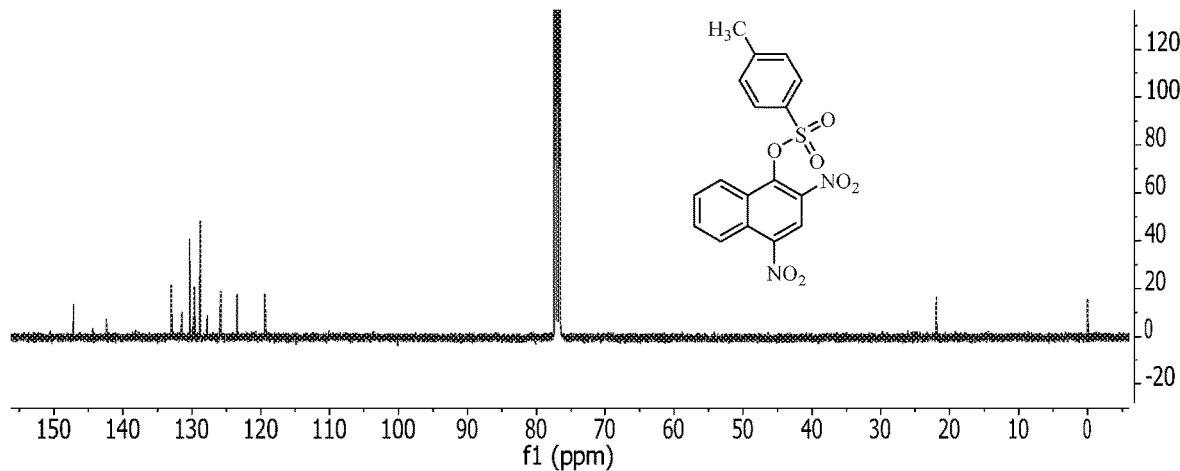

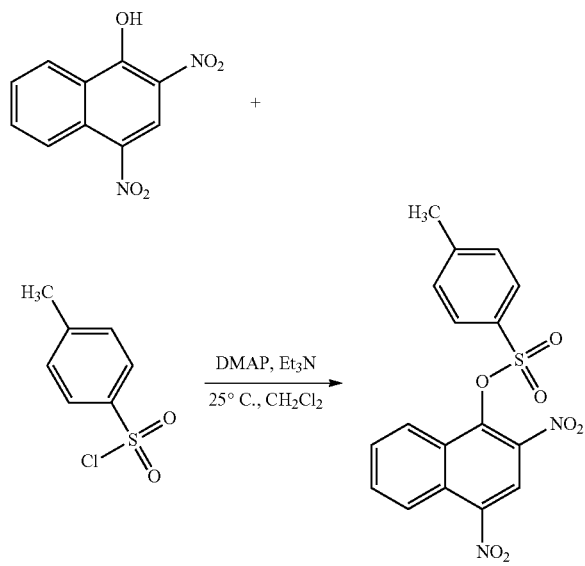

p-Toluenesulfonic acid (152.9 mg, 0.802 mmol) was added dropwise to a solution of 2,4-dinitronaphth-1-ol (170.8 mg, 0.729 mmol), triethylamine (112 µL, 0.802 mmol), and DMAP (8.9 mg, 0.073 mmol) in $CH_2Cl_2$ (2 mL) at room temperature. After the reaction was complete, the mixture was washed with water and extracted with $CH_2Cl_2$. The combined organic layers were dried over $MgSO_4$ and concentrated in vacuo. Purification by flash column chromatography on silica gel (20% EtOAc in hexanes followed by 10% MeOH in $CH_2Cl_2$) afforded 137.2 mg (0.35 mmol, 55%) of a yellow solid. $^1$H NMR (400 MHz, $CDCl_3$): δ=8.76 (s, 1H), 8.62 (dd, J=8.9, 0.9 Hz, 1H), 8.35 (dd, J=8.7, 1.0 Hz, 1H), 7.93 (ddd, J=8.4, 7.0, 1.3 Hz, 1H), 7.90-7.87 (m, 2H), 7.76 (ddd, J=8.3, 7.0, 1.1 Hz, 1H), 7.49-7.39 (m, 2H), 2.52 (s, 3H). $^{13}$C NMR (100 MHz, $CDCl_3$): δ=21.9, 119.4, 123.5, 125.8, 127.8, 128.8, 129.7, 129.8, 130.4, 131.5, 133.0, 142.4, 144.4, 147.2. Anal. Calcd. for $C_{17}H_{12}N_2O_7S$: C, 52.58; H, 3.11; N, 7.21. Found: C, 52.72; H, 3.41; N, 6.82. See FIGS. 7A-B.

Synthesis of N,S-bis(2,4-dinitrophenyl)cysteine (4)

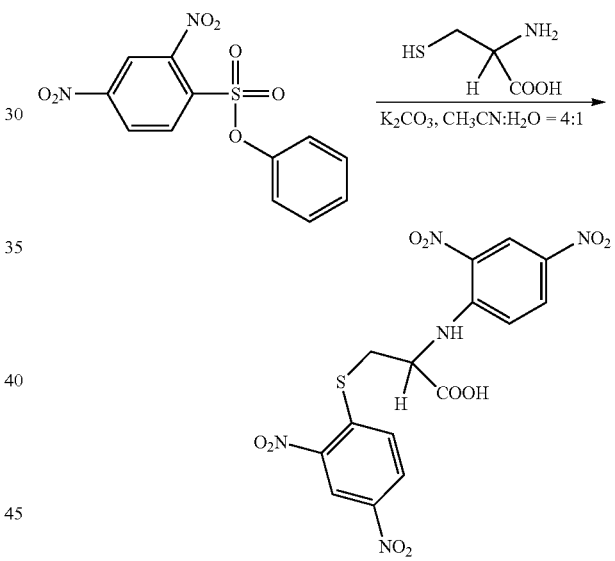

Figure 8A:
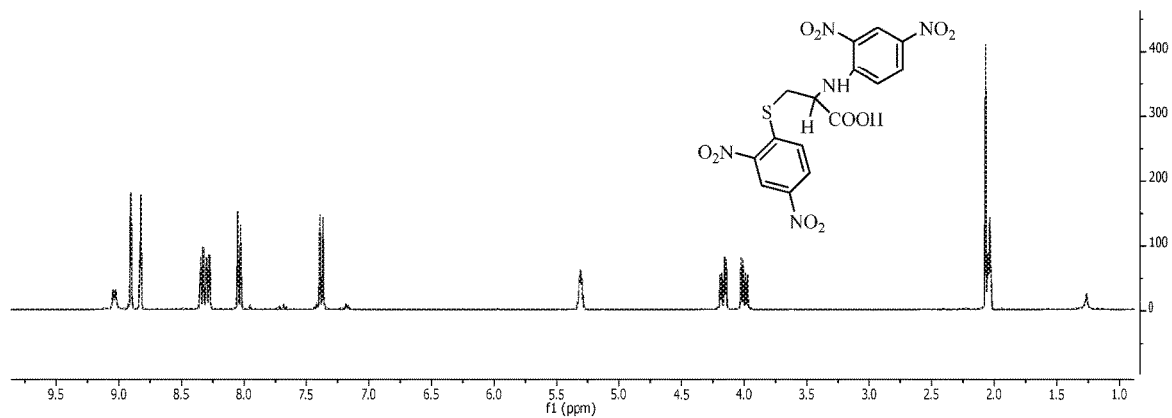
FIGS. 8A-B are the ¹H NMR (FIG. 8A) and ¹³C NMR (FIG. 8B) spectra of N,S-bis(2,4-dinitrophenyl)cysteine in $(CD_3)_2CO$.
Figure 8B:
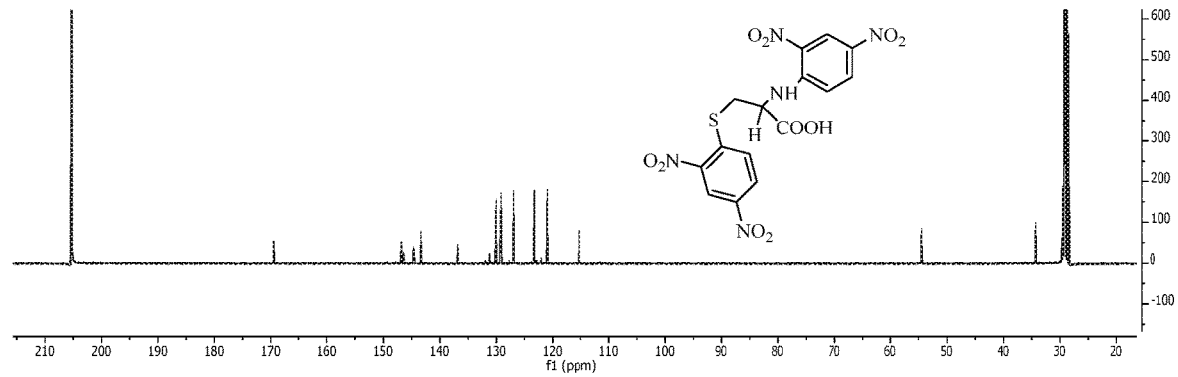
Figure 9:
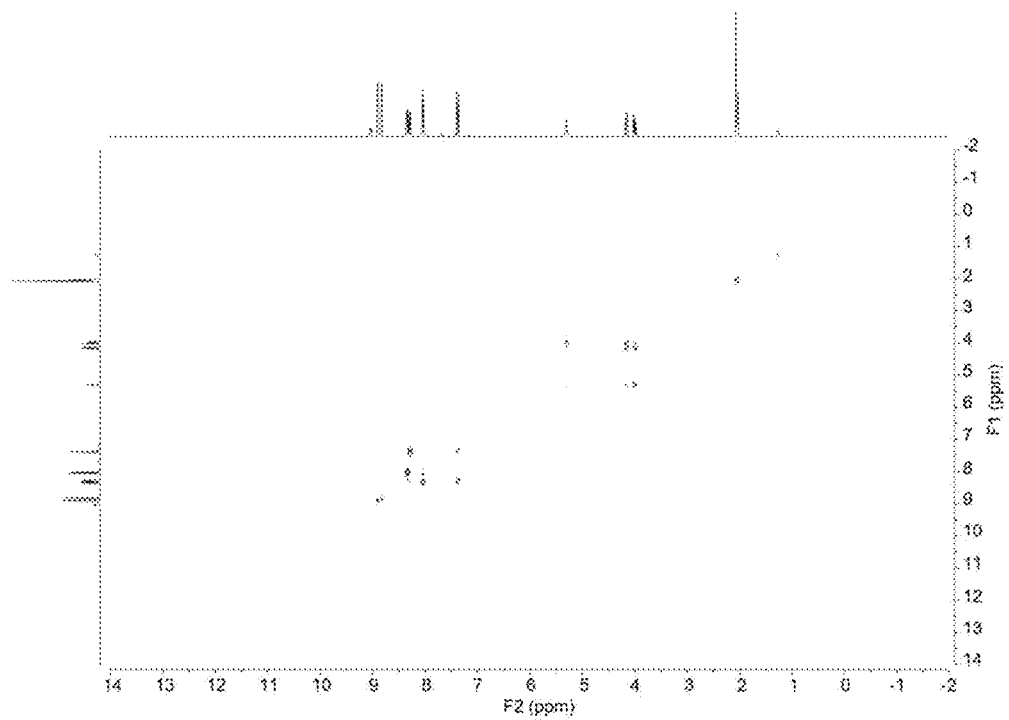
FIG. 9 is the COSY spectrum of N,S-bis(2,4-dinitrophenyl)cysteine in $(CD_3)_2CO$.
Figure 10:
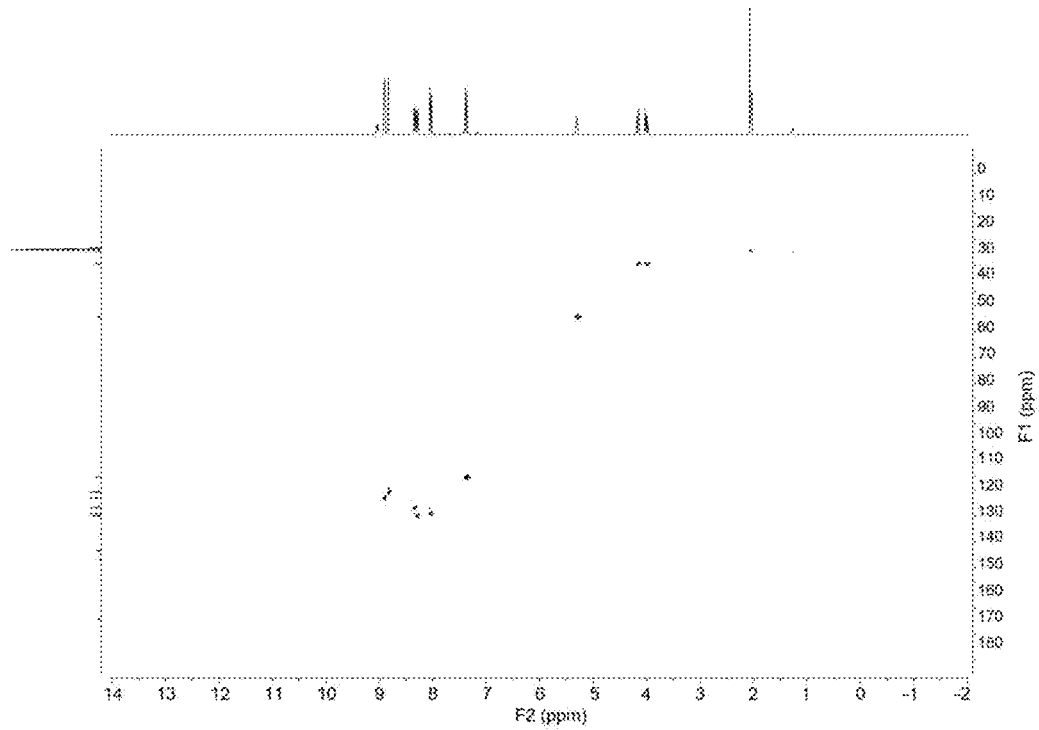
FIG. 10 is the HSQC spectrum of N,S-bis(2,4-dinitrophenyl)cysteine in $(CD_3)_2CO$.
Figure 11:
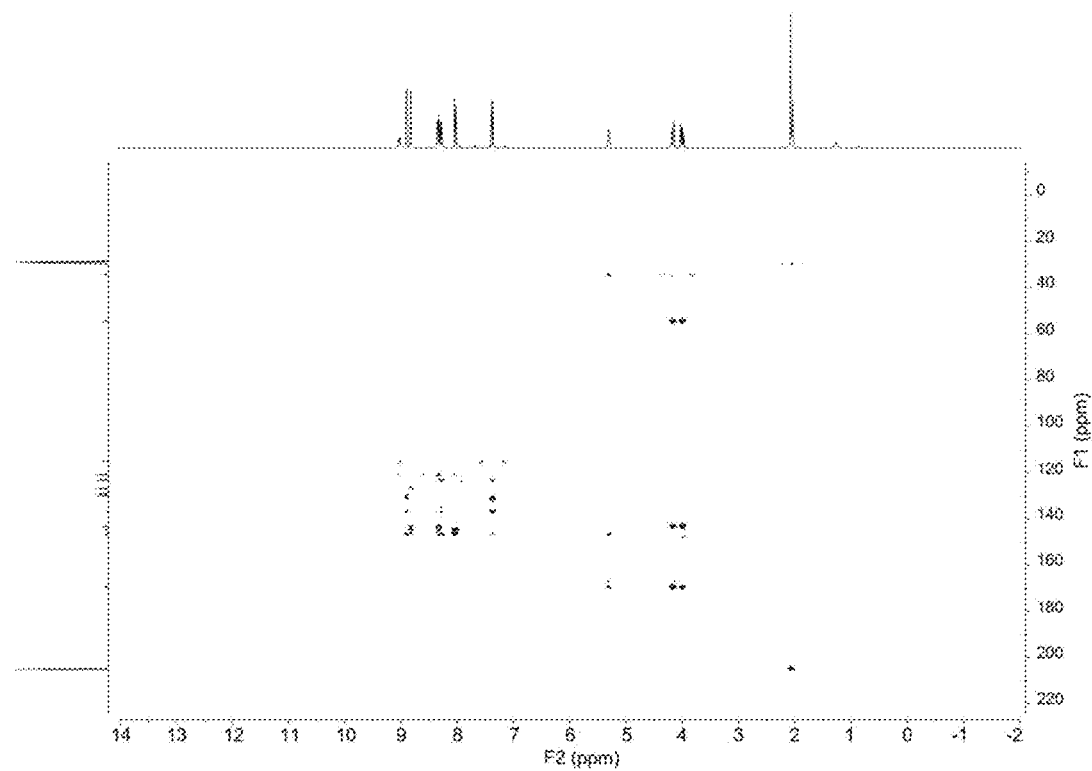
FIG. 11 is the HMBC spectrum of N,S-bis(2,4-dinitrophenyl)cysteine in $(CD_3)_2CO$.
Figure 12:
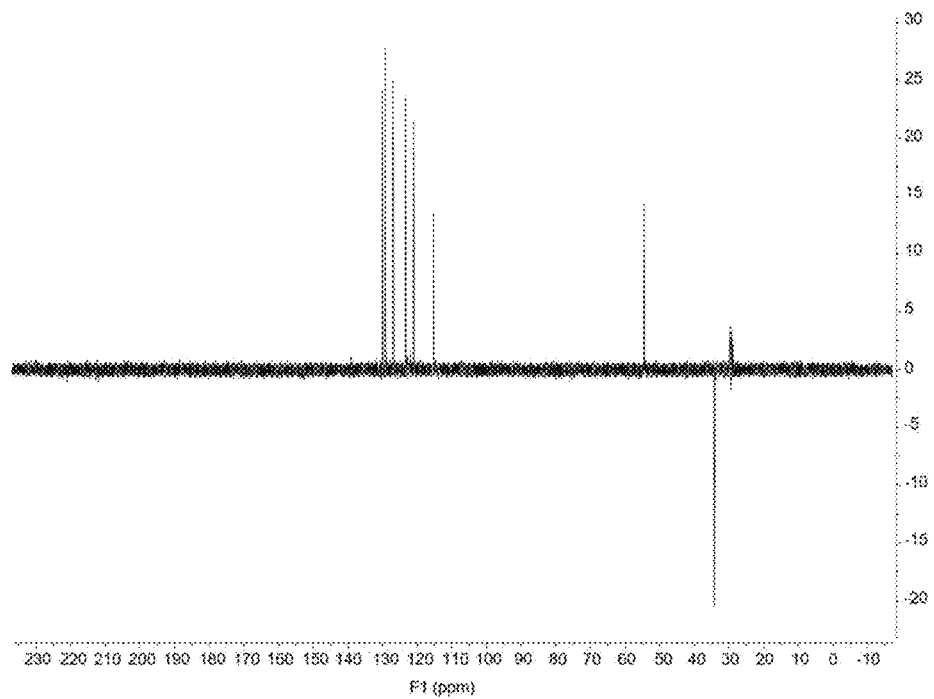
FIG. 12 is the DEPT spectrum of N,S-bis(2,4-dinitrophenyl)cysteine in $(CD_3)_2CO$.
Figure 13:
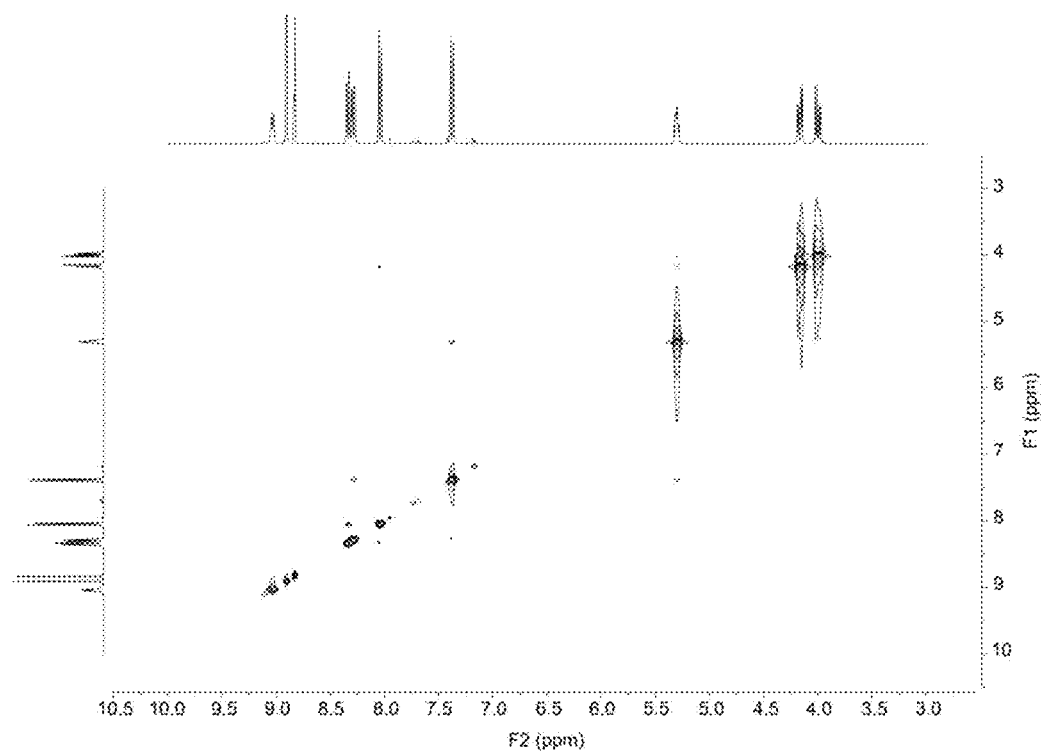
FIG. 13 is the NOESY spectrum of N,S-bis(2,4-dinitrophenyl)cysteine in $(CD_3)_2CO$.

A solution of phenyl 2,4-dinitrobenzenesulfonate (1) (100.0 mg, 0.309 mmol) in 2 mL of $CH_3CN$ was added to a mixture of cysteine (18.7 mg, 0.154 mmol) and $K_2CO_3$ (85.1 mg, 0.616 mmol) in 0.5 mL of deionized water at room temperature. After the reaction was complete, the mixture was concentrated in vacuo. Column purification on silica gel using 100% ethyl acetate followed by 5% formic acid in ethyl acetate as mobile phase afforded 49.9 mg (110 pMol, 72%) of an amorphous yellow solid. $^1$H NMR (400 MHz, $(CD_3)_2CO$) δ=9.04 (d, J=7.7 Hz, 1H), 8.90 (d, J=2.7 Hz, 1H), 8.83 (d, J=2.5 Hz, 1H), 8.34 (dd, J=9.0, 2.5 Hz, 1H), 8.29 (dd, J=9.5, 2.7 Hz, 1H), 7.38 (d, J=9.5 Hz, 1H), 5.31 (m, 1H), 4.17 (dd, J=14.0, 4.4 Hz, 1H), 4.00 (dd, J=14.0, 6.3 Hz, 1H). $^{13}$C NMR (100 MHz, $CD_3)_2CO$) δ=34.3, 54.5, 115.3, 120.9, 123.3, 127.0, 129.2, 130.0, 136.9, 143.3, 144.6, 146.4, 146.8, 146.9, 169.5. See FIGS. 8A-B. (See also FIGS. 9-13 for COSY, HSQC, HMBC, DEPT, and NOESY spectra, respectively.)

Example 3-Crystallographic Analysis

Phenyl 2,4-dinitrobenzenesulfonate (1)

Figure 14:
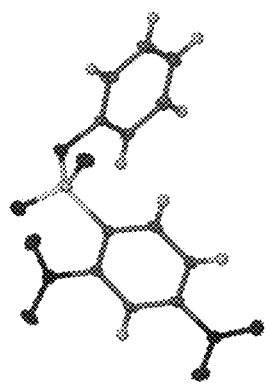
FIG. 14 shows the crystal structure of probe 1.

A single crystal was obtained by slow evaporation of a solution of phenyl 2,4-dinitrobenzenesulfonate in $CH_3CN$. Single crystal X-ray analysis was performed at 296 K using a Siemens platform diffractometer with graphite monochromated Mo-Kα radiation (λ=0.71073 Å). Data were integrated and corrected using the Apex 2 program. The structures were solved by direct methods and refined with full-matrix least-square analysis using SHELX-97-2 software. Non-hydrogen atoms were refined with anisotropic displacement parameter. Crystal data: $C_{12}H_8N_2O_7S$, M=324.26, colorless needle, 0.8×0.6×0.3 mm$^3$, orthorhombic, space group $P2_12_1$, a=6.2524(10), b=10.8770(18), c=19.422(3) Å, V=1320.8(4) Å$^3$, Z=4. Absolute structure parameter is not given since crystal was achiral that crystallized in a chiral space group. The crystal structure of probe 1 is shown in FIG. 14.

2,4-Dinitronaphthalen-1-yl methanesulfonate (2)

Figure 15:
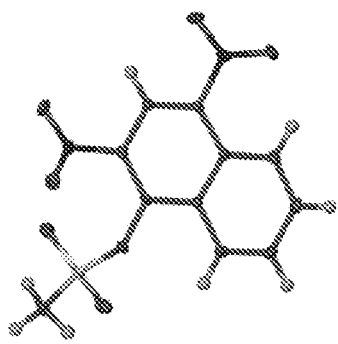
FIG. 15 shows the crystal structure of probe 2.

A single crystal was obtained by slow evaporation of a solution of 2,4-dinitronaphthalen-1-yl methanesulfonate in $CHCl_3$. Single crystal X-ray analysis was performed at 100 K using a Siemens platform diffractometer with graphite monochromated Mo-Kα radiation (λ=0.71073 Å). Data were integrated and corrected using the Apex 2 program. The structures were solved by direct methods and refined with full-matrix least-square analysis using SHELX-97-2 software. Non-hydrogen atoms were refined with anisotropic displacement parameter. Crystal data: $C_{11}H_8N_2O_7S$, M=312.25, colorless needle, 0.4×0.7×0.9 mm$^3$, monoclinic, space group $P2_1/c$, a=9.3945(5), b=16.2435(8), c=8.0481(4) Å, V=1226.89(11) Å$^3$, Z=4. The crystal structure of probe 2 is shown in FIG. 15.

2,4-Dinitronaphthalen-1-yl 4-toluenesulfonate (3)

Figure 16:
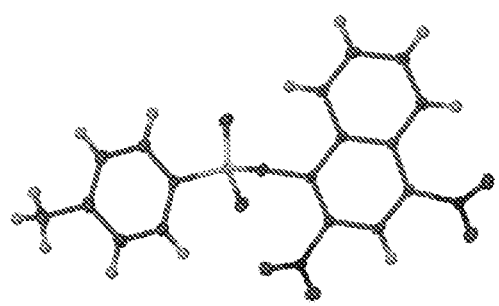
FIG. 16 shows the crystal structure of probe 3.

A single crystal was obtained by slow evaporation of a solution of 2,4-dinitronaphthalen-1-yl 4-toluenesulfonate in $CHCl_3$. Single crystal X-ray analysis was performed at 173 K using a Siemens platform diffractometer with graphite monochromated Mo-Kα radiation (λ=0.71073 Å). Data were integrated and corrected using the Apex 2 program. The structures were solved by direct methods and refined with full-matrix least-square analysis using SHELX-97-2 software. Non-hydrogen atoms were refined with anisotropic displacement parameter. Crystal data: $C_{17}H_{12}N_2O_7S$, M=388.35, colorless needle, 0.3×0.5×1.0 mm$^3$, monoclinic, space group $P2_1/c$, a=12.8942(15), b=7.7595(9), c=16.4720(19) Å, V=1647.7(3) Å$^3$, Z=4. The crystal structure of probe 3 is shown in FIG. 16.

Example 4-Probe Selection and Sensing Development

Experimental Procedures

Generally.

Initially, reactions were performed with 1.25 mM cysteine concentrations as described below to identify a probe with superior chiroptical properties. The CD spectra of the diluted solutions (110 μM) were collected with a standard sensitivity of 100 mdeg, a data pitch of 0.5 nm, a bandwidth of 1 nm, in a continuous scanning mode with a scanning speed of 500 nm/min and a response of 1 s, using a quartz cuvette (1 cm path length). The data were baseline corrected and smoothed using a binomial equation. UV spectra were collected with an average scanning time of 0.0125 s, a data interval of 5.00 nm, and a scan rate of 400 nm/s.

Cysteine Sensing Using phenyl 2,4-dinitrobenzenesulfonate (1)

Figure 17:
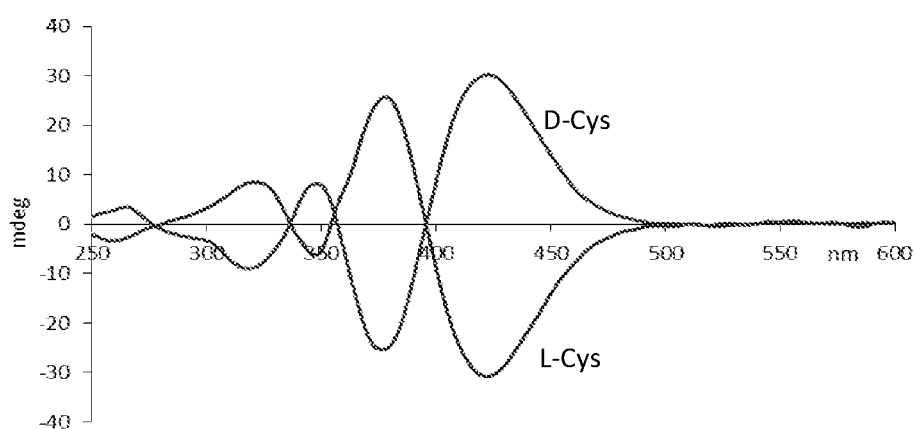
FIG. 17 is the CD spectra obtained using probe 1 with L-cysteine and D-cysteine. CD measurements were taken at 110 μM in acetonitrile.

A solution of phenyl 2,4-dinitrobenzenesulfonate (1) (2.50 mM, 2.43 mg), cysteine (1.25 mM, 0.45 mg), and $K_2CO_3$ (5 mM, 2.07 mg) in 3 mL of $CH_3CN$:water (4:1) was stirred for 1 hour. To 200 μL of this solution acetonitrile (2 mL) was added and the mixture was subjected to CD analysis (110 μM) (FIG. 1B (left) and FIG. 17). Control experiments with cysteine in the absence of the probe did not show any CD signal at the wavelengths of interest.

Cysteine Sensing Using 2,4-dinitronaphthalen-1-yl methanesulfonate (2)

Figure 18:
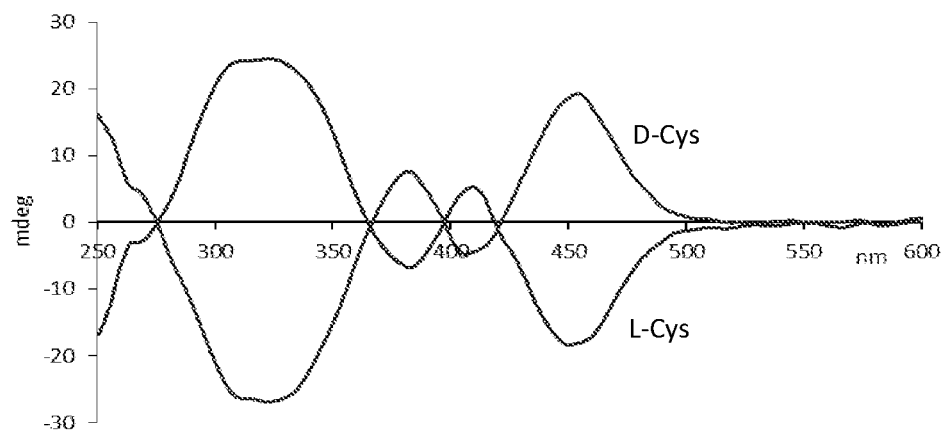
FIG. 18 is the CD spectra obtained using probe 2 with L-cysteine and D-cysteine. CD measurements were taken at 110 μM in acetonitrile.

A solution of 2,4-dinitronaphthalen-1-yl methanesulfonate (2) (2.50 mM, 2.34 mg), cysteine (1.25 mM, 0.45 mg), and $K_2CO_3$ (5 mM, 2.07 mg) in 3 mL of $CH_3CN$:water (4:1) was stirred for 1 hour. To 200 μL of this solution acetonitrile (2 mL) was added and the mixture was subjected to CD analysis (110 μM) (FIG. 18). Control experiments with cysteine in the absence of the probe did not show any CD signal at the wavelengths of interest.

Cysteine Sensing Using 2,4-dinitronaphthalen-1-yl 4-toluenesulfonate (3)

A solution of 2,4-dinitronaphthalen-1-yl-4-toluenesulfonate (3) (2.50 mM, 2.91 mg), cysteine (1.25 mM, 0.45 mg), and $K_2CO_3$ (5 mM, 2.07 mg) in 3 mL of $CH_3CN$:water (4:1) was stirred for 1 hour. To 200 μL of this solution acetonitrile (2 mL) was added and the mixture was subjected to CD analysis (110 μM) (FIG. 1B (right) and FIG. 19). Control experiments with cysteine in the absence of the probe did not show any CD signal at the wavelengths of interest.

Figure 20:
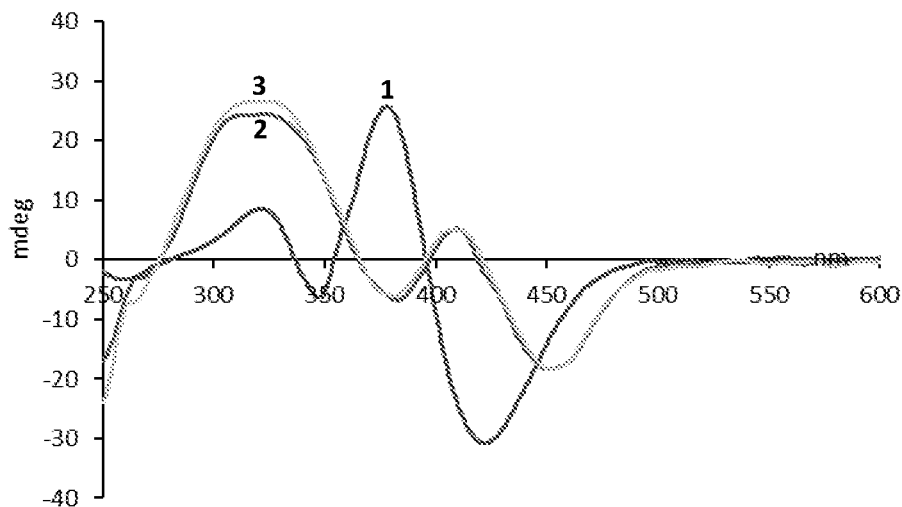
FIG. 20 shows a comparison of the CD spectra obtained with L-cysteine and probes 1-3. All CD measurements were taken at 110 μM in acetonitrile.

A comparison of the CD spectra obtained with L-cysteine and probes 1-3 is shown in FIG. 20.

Solvent and Base Optimization.

Figure 21:
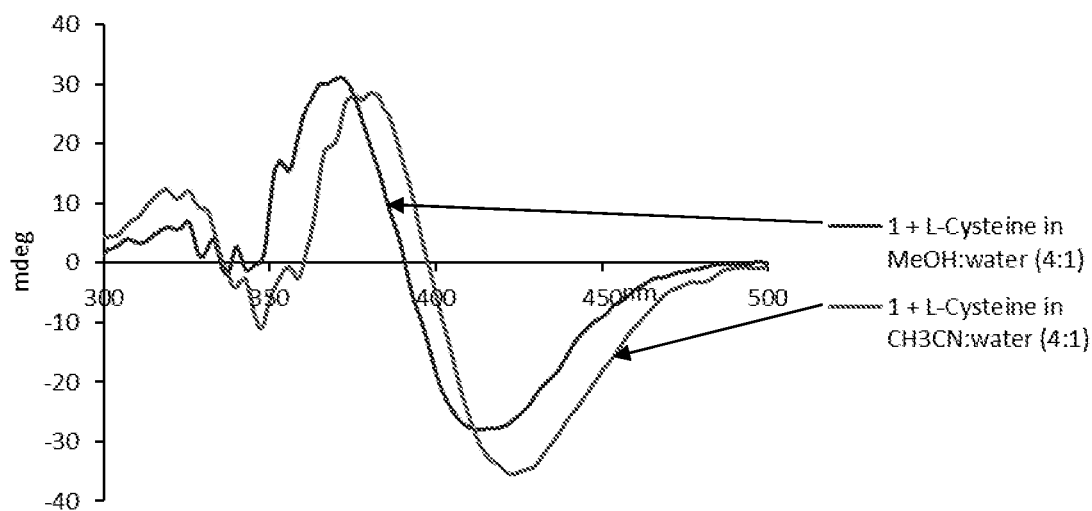
FIG. 21 is the CD spectra showing CD sensing of L-cysteine with probe 1 in different solvents.
Figure 22:
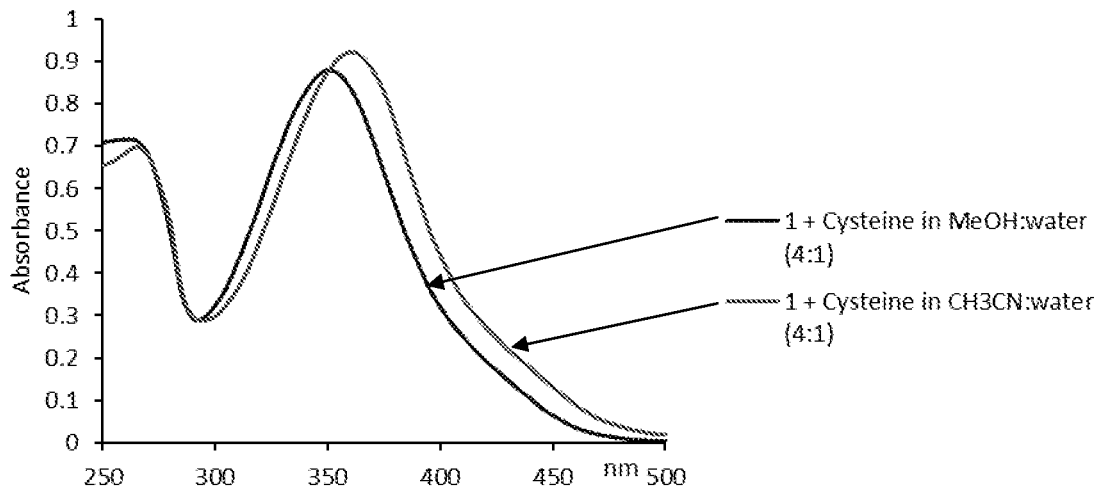
FIG. 22 is the UV spectra showing the comparison of L-cysteine UV sensing with probe 1 in different solvents.

A solution of probe 1 (3.33 mM, 3.24 mg), L-cysteine (1.66 mM, 0.61 mg), and TBAOH (6.67 mM, 5.19 mg) in 3 mL of $CH_3CN$:water (4:1) was stirred for 1 hour. To 150 μL of this solution acetonitrile (2 mL) was added and the mixture was subjected to CD analysis (110 μM) (FIG. 21). To 50 μL of this solution acetonitrile (2 mL) was added and the mixture was subjected to UV analysis (50 μM) (FIG. 22). The above experiment was repeated in MeOH:water (4:1) and subjected to CD and UV analysis (110 μM and 50 μM respectively) (FIGS. 21 and 22).

Figure 2A:
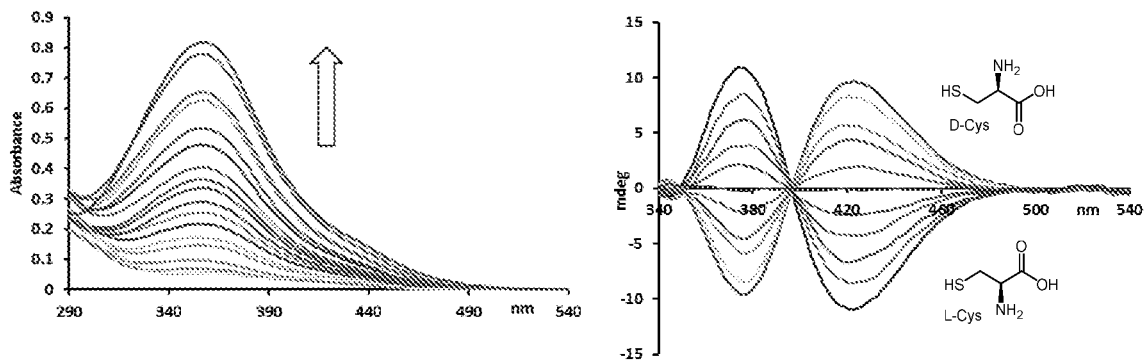
FIGS. 2A-C relate to chiroptical cysteine sensing and reaction analysis.

A solution of probe 1 (3.33 mM, 3.24 mg), L-cysteine (1.66 mM, 0.61 mg), and TBAOH (6.67 mM, 5.19 mg) in 3 mL of $CH_3CN$:water (4:1) was stirred for 1 hour. To 150 μL of this solution acetonitrile (2 mL) was added and the mixture was subjected to CD analysis (110 μM) (FIG. 20). The above experiment was repeated with KOH, NaOH, LiOH, $Na_2CO_3$, $Cs_2CO_3$, $K_2CO_3$, and DBU as base and subjected to CD analysis (110 μM) (FIG. 2C).

Figure 23:
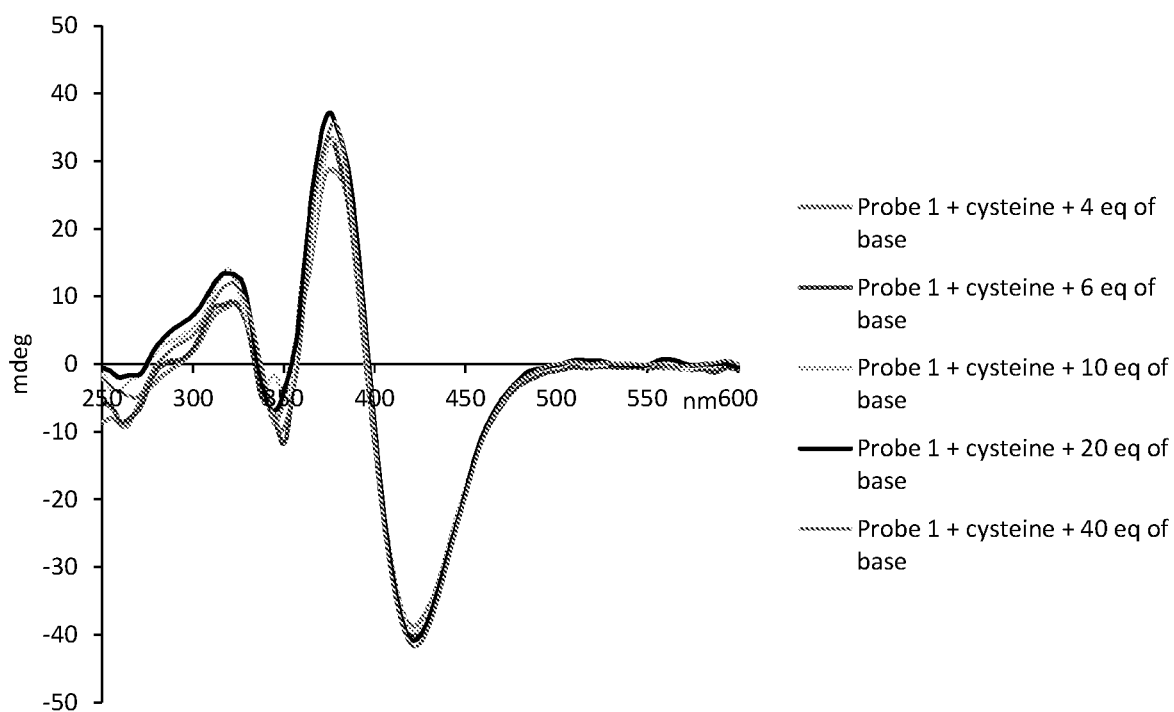
FIG. 23 is the CD spectra showing sensing of L-cysteine in the presence of varying amounts of $K_2CO_3$.

A solution of probe 1 (2.5 mM, 2.43 mg), L-cysteine (1.25 mM, 0.45 mg), and varying amount (4, 6, 10, 20, 40 equivalents) of $K_2CO_3$ in 3 mL of $CH_3CN$:water (4:1) was stirred for 1 hour. To 250 µL of these solutions acetonitrile (2 mL) was added and the mixtures were subjected to CD analysis (140 µM) (FIG. 23).

The base screening experiments revealed that superior CD sensing results are obtained using $K_2CO_3$, KOH, NaOH, and DBU. Using the base in larger excess did not significantly change the CD response of the probe to cysteine.

Results and Discussion

A molecular probe design was favored that would allow fast cysteine detection and generate independent UV and circular dichroism (CD) data for simultaneous determination of a total of three variables: absolute configuration, enantiomeric composition, and overall concentration of the combined enantiomers in aqueous solution. It was envisioned that this could be accomplished by the attachment of two chromophores, such as aryl moieties, onto the thiol and amino groups in cysteine. The incorporation of two proximate chromophores would afford a distinct circular dichroism signal that is indicative of the absolute configuration of the major enantiomer (based on the sign of the produced Cotton effect) and also provide the means for er analysis (based on the induced CD amplitude). In contrast with this enantioselective sensing mode, a concomitant colorimetric or UV change would be independent of the sample er and therefore suitable for quantification of the total amount of the sensing target. Since modern instruments automatically produce UV and CD spectra at the same time, a dual UV/CD sensing method seemed particularly practical and convenient.

In the search for a rugged chiroptical sensing assay that is specific to cysteine a covalent derivatization approach with a chromophoric probe that would generate strong spectroscopic readouts at high wavelengths to avoid interference with other compounds, in particular amino acids, for quantitative analysis at biologically relevant concentrations was favored. Specifically, an inexpensive readily available small-molecule probe that combines good solubility and hydrolytic stability for use in aqueous media with sufficient reactivity for fast cysteine detection and chirality recognition even at micromolar levels and at room temperature was sought. The screening of several molecular receptors and binding motifs, including Schiff base formation and metal complexation, led to investigation of the possibility of complementary N- and S-arylation of the amino and thiol functionalities in cysteine using phenyl 2,4-dinitrobenzenesulfonate, 1, and the 2,4-dinitronaphthalene analogues 2 and 3 (see FIG. 1A). The release of fluorescent indicators via nucleophilic aromatic substitution at a covalently linked dinitrobenzene scaffold has been used for indirect cysteine analysis. (Maeda et al., *Angew. Chem. Int. Ed.* 44:2922-2925 (2005); Jiang et al., *Angew. Chem. Int. Ed.* 46:8445-8448 (2007); Maeda et al., *Angew. Chem. Int. Ed.* 45:1810-1813 (2006); Bouffard et al., *Org. Lett.* 10:37-40 (2008); Shibata et al., *Bioorg. Med. Chem. Lett.* 18:2246-2249 (2008); Ji et al., *J. Org. Chem.* 74:4855-4865 (2009); Athanasiou-Malaki & Koupparis, *Analyst* 112:757-761 (1987) (potentiometric amino acid detection), each of which is hereby incorporated by reference in its entirety.) The three sulfonates were prepared in a single step from the corresponding phenol and naphthol precursors and fully characterized by NMR spectroscopy, crystallography, and combustion analysis (see Examples 2-3).

Figure 1B:
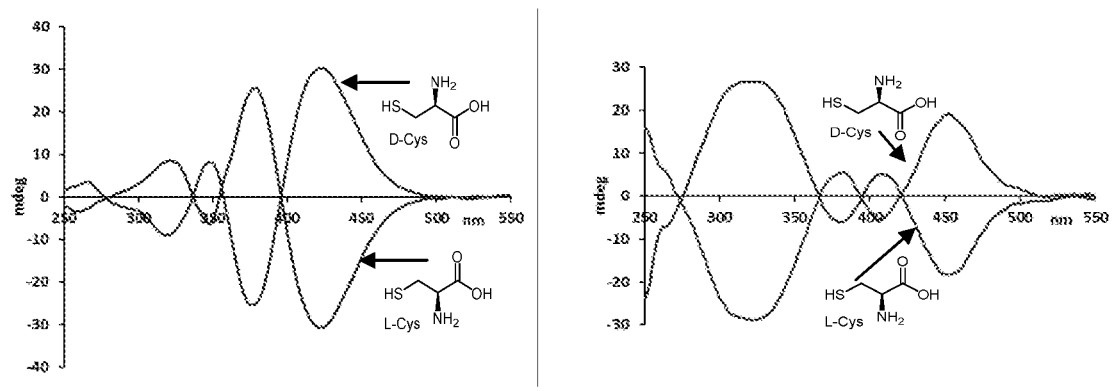
Figure 19:
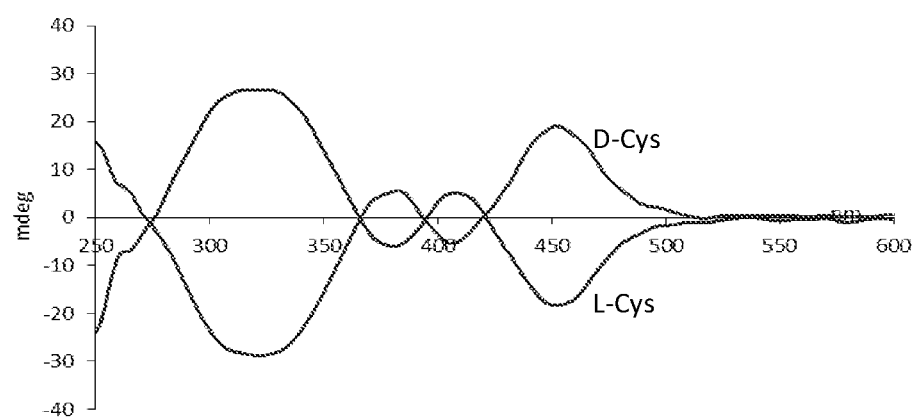
FIG. 19 is the CD spectra obtained using probe 3 with L-cysteine and D-cysteine. CD measurements were taken at 110 μM in acetonitrile.

Initial evaluation of the cysteine sensing potential of 1-3 revealed strong ultraviolet and CD readouts above 300 nm at approximately 100 µM concentrations using aqueous acetonitrile as solvent (see, e.g., FIG. 1B). The probes are stable to hydrolysis even under basic conditions and the intended double ipso-substitution reaction with cysteine was found to generate characteristic CD signals that identify the absolute configuration of the substrate. The sensing of D-cysteine consistently gave two positive Cotton effects, the first in the 400 nm region and a second above 300 nm. The opposite trend was observed with the L-enantiomer. The derivatization with probes 2 and 3 yields the same cysteine analogue and virtually identical CD responses were obtained in these cases as expected (FIGS. 18 and 19). Although all three probes showed substantial promise, probe 1 was observed to afford the strongest CD amplitude above 400 nm under the same conditions, which is preferable with regard to the sensitivity and ruggedness of the planned quantitative ee sensing applications, vide infra.

Example 5-Optimization of the Chiroptical Assay

Mechanistic Studies

Identification of the Sensing Product.

The solubility of the sensing product was determined to be 65 mg/mL (ACN:water=1:1). CD analysis was performed with 1.25 mM cysteine solutions and probe 1. The CD spectra were collected with a standard sensitivity of 100 mdeg, a data pitch of 0.5 nm, a bandwidth of 1 nm, in a continuous scanning mode with a scanning speed of 500 nm/min and a response of 1 s, using a quartz cuvette (1 cm path length). The data were baseline corrected and smoothed using a binomial equation. UV spectra were collected with an average scanning time of 0.0125 s, a data interval of 5.00 nm, and a scan rate of 400 nm/s.

Figure 25A:
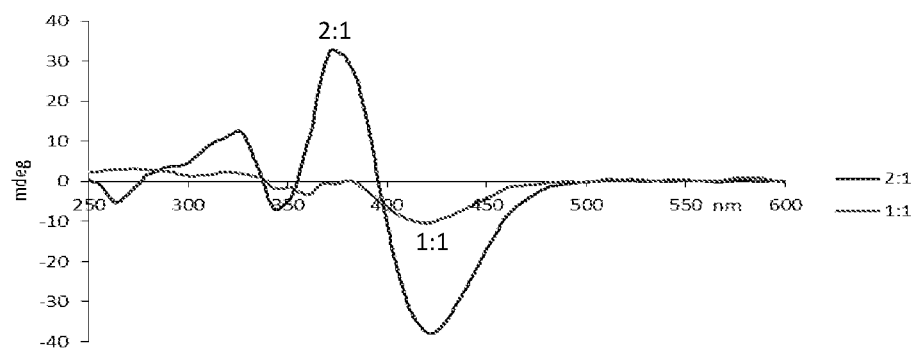
FIGS. 25A-B are the CD spectra (FIG. 25A) and UV spectra (FIG. 25B) obtained of reaction mixtures with a 1:1 or 2:1 probe:cysteine ratio. CD measurements were taken at 140 μM in acetonitrile. UV measurements were taken at 30 μM in acetonitrile. (Reaction mixtures: 1 equivalent ("1:1") or 2 equivalents ("2:1") of probe 1 with L-cysteine and $K_2CO_3$ in $CH_3CN$:water (4:1).)
Figure 25B:
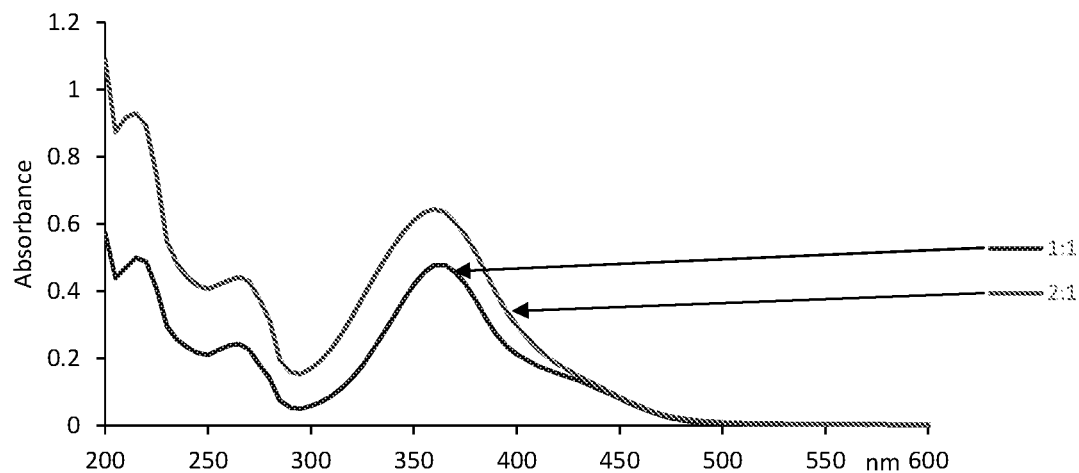

It was expected that both the thiol and the amino group in cysteine react and consume two equivalents of the probe. The reactivity of the two sites towards the probe was analyzed by reacting 1 equivalent of probe 1 (1.25 mM) with L-cysteine (1.25 mM) and $K_2CO_3$ (5 mM) in 3 mL of $CH_3CN$:water (4:1). A second reaction was performed using 2 equivalents of the probe (2.50 mM) with L-cysteine (1.25 mM) and $K_2CO_3$ (5 mM) in 3 mL of $CH_3CN$:water (4:1). The resulting mixtures were analyzed by CD and UV spectroscopy at 140 µM and 30 µM, respectively (FIGS. 25A-B).

Figure 26:
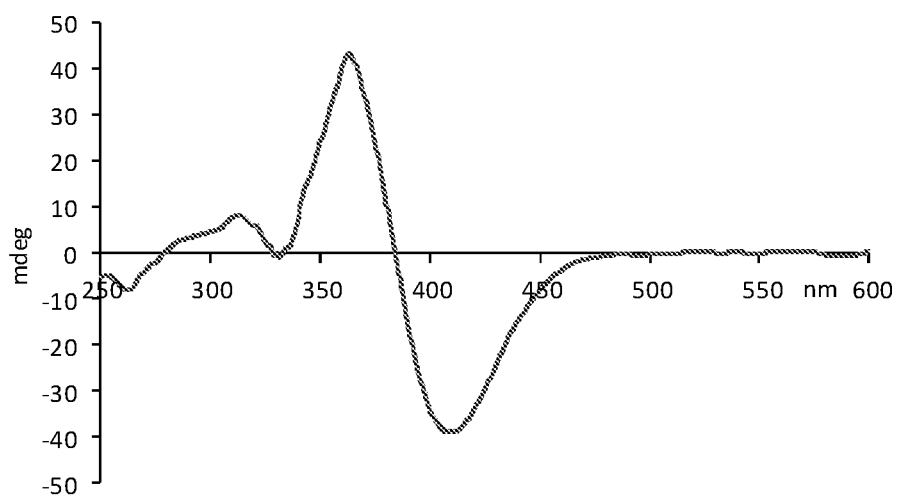
FIG. 26 is the CD spectra showing sensing of synthesized N,S-bis(2,4-dinitrophenyl)cysteine from probe 1 and L-cysteine. CD measurements were taken at 240 μM in acetonitrile.

For comparison, N,S-bis(2,4-dinitrophenyl)cysteine was synthesized from probe 1 and L-cysteine. CD analysis with this derivative confirmed that cysteine reacts with two equivalents of the probe and forms N,S-bis(2,4-dinitrophenyl)cysteine (FIG. 26).

Reaction Analysis.

Figure 27:
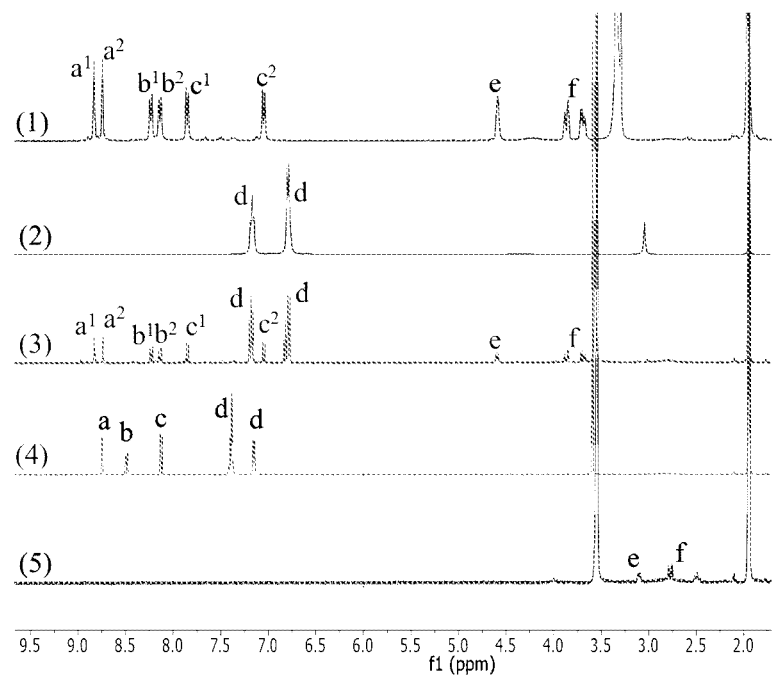
FIG. 27 is the ¹H NMR spectra relating to the analysis of probe 1 and L-cysteine. (1) N,S-bis(2,4-dinitrophenyl)cysteine; isolated product of the reaction between L-cysteine and 2 equivalents of probe 1 (in the presence of 4 equivalents of $K_2CO_3$); (2) Phenol in the presence of 4 equivalents of $K_2CO_3$; (3) Reaction mixture of L-cysteine with 2 equivalents of probe 1 in the presence of 4 equivalents of $K_2CO_3$, after 7 minutes; (4) Probe 1 in the presence 4 equivalents of $K_2CO_3$; (5) L-cysteine in the presence of 4 equivalents of $K_2CO_3$.

The reaction between L-cysteine (1.25 mM) and probe 1 (2.50 mM) in the presence of $K_2CO_3$ (5.0 mM) in 0.85 mL of in $CD_3CN:D_2O$ (4:1) was monitored by $^1H$ NMR (FIG. 27). The reaction was complete within 10 minutes under these conditions.

Figure 24A:
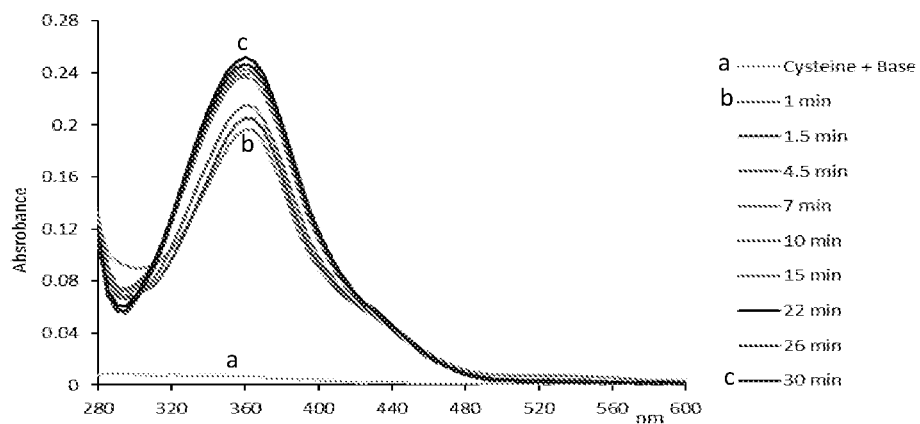
FIGS. 24A-B relate to the reaction between cysteine and probe 1 over time.

The cysteine binding (at 1.25 mM) with probe 1 (2.50 mM) in the presence of $K_2CO_3$ (5.0 mM) in 6 mL of $CH_3CN$:water (4:1) was monitored using UV-Vis spectroscopy (FIG. 24A). Measurements were taken at 10 µM concentration, after dilution of 20 µL reaction mixture aliquots with 2 mL of acetonitrile. The reaction was complete within 10 minutes under these conditions.

Racemization Analysis.

Figure 28:
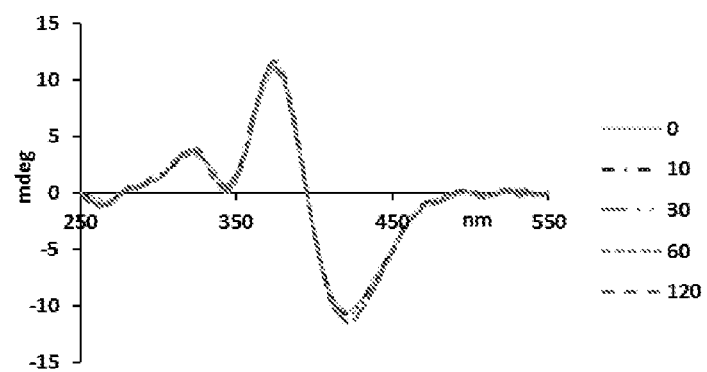
FIG. 28 is the CD spectra of the sensing mixture at 0, 10, 30, 60, and 120 minutes.

CD measurements of the sensing mixture using the typical conditions described above (35 µM and $K_2CO_3$ as base) were taken at 0, 10, 30, 60, and 120 minutes (FIG. 28). There was no sign of product racemization.

Figure 29:
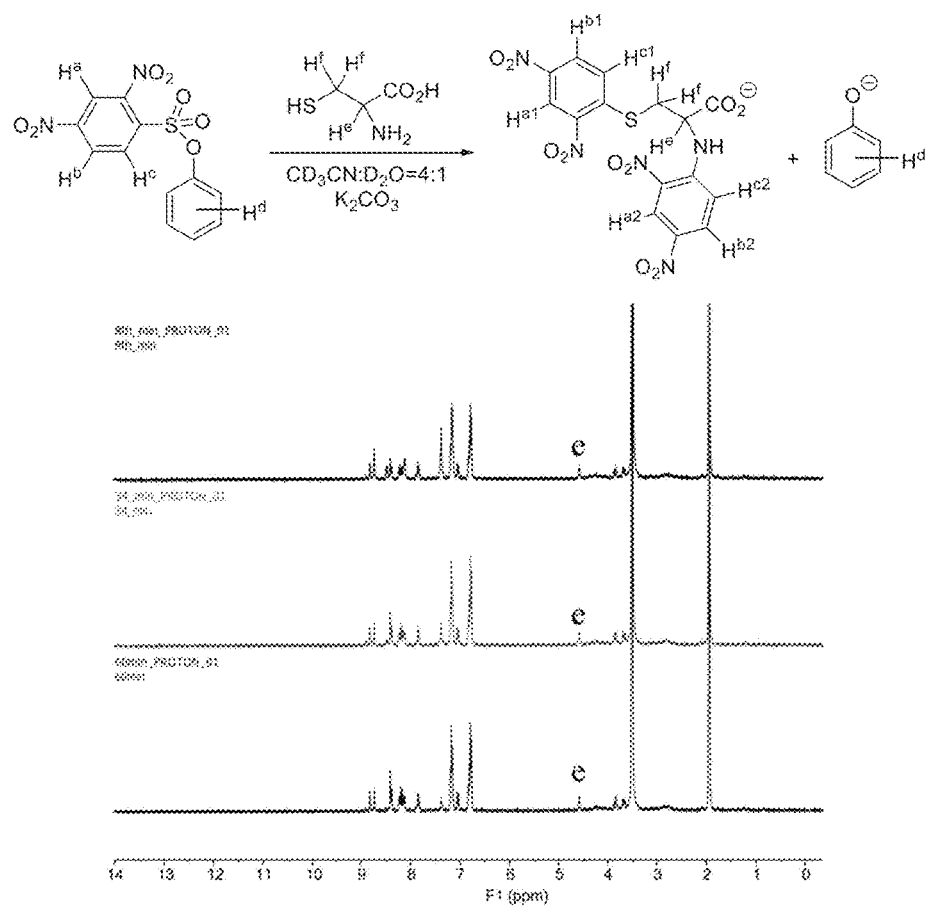
FIG. 29 is the ¹H NMR spectra showing continued ¹H NMR analysis of the sensing mixture.

Continued NMR analysis of the sensing mixture under the conditions used in the NMR study shown above (1.25 mM) showed no sign of H/D exchange for the proton $H^e$ attached to the chiral carbon atom in 4 (FIG. 29). The integration of the peak for H$^e$ remained constant after 1 hour.

Linearity Study at Higher Concentration.

Figure 30A:
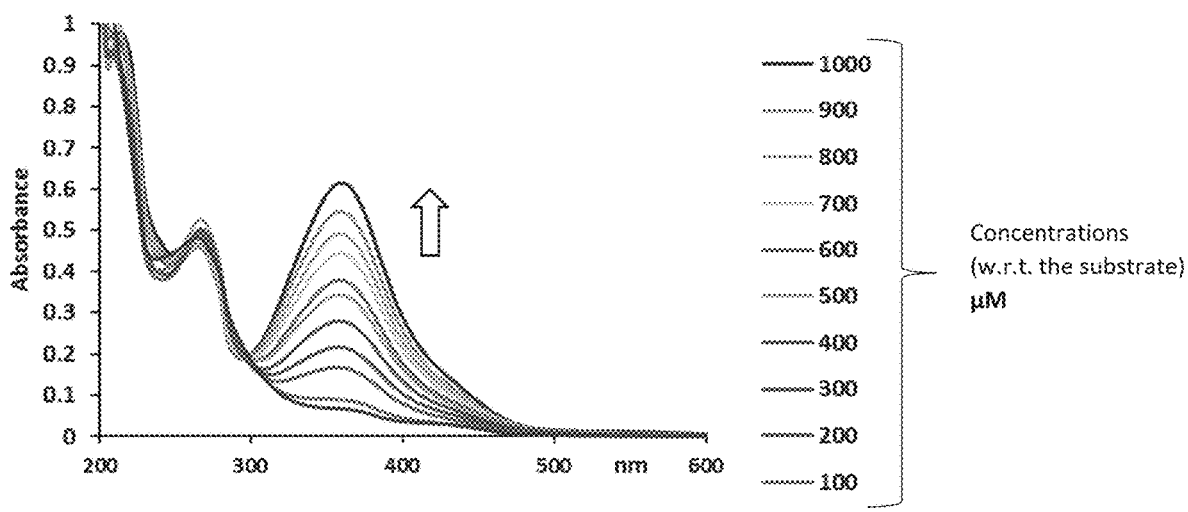
FIGS. 30A-B are the UV spectra (FIG. 30A) showing the UV response of probe 1 measured over a cysteine concentration range from 100 to 100 μM and a plot (FIG. 30B) of the UV absorbance at 355 nm.

The UV response of probe 1 was measured over a cysteine concentration range from 100 to 1000 μM (FIG. 30A).

Figure 30B:
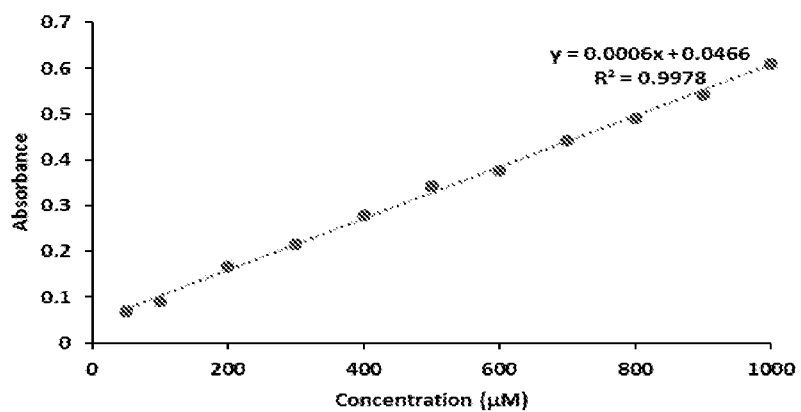

Plotting of the UV absorbance at 355 nm showed a linear sensor response, which indicates the absence of aggregation and self-recognition effects (FIG. 30B).

Results and Discussion

Figure 24B:
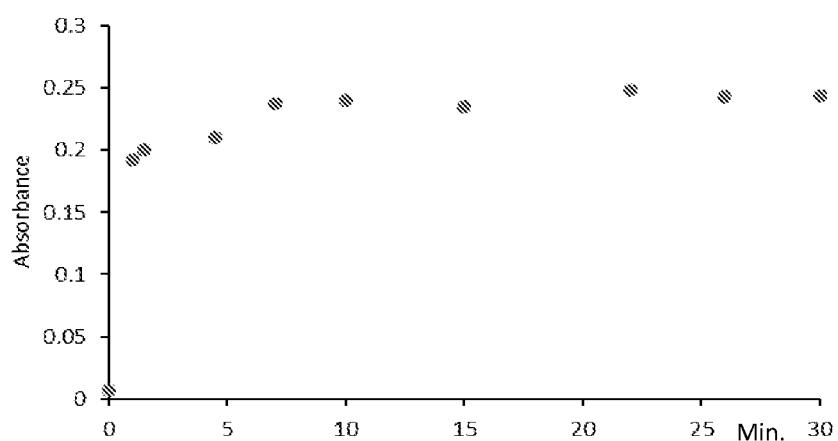

Based on the preliminary results discussed in Example 4, optimization of the chiroptical sensing using 1 as probe continued. To provide evidence that indeed both the amino and the thiol group in Cys undergo ipso-substitution, N,S-bis(2,4-dinitrophenyl)cysteine, 4, was prepared and the structure was identified by one- and two-dimensional NMR spectroscopy (FIGS. 8A-B and FIGS. 9-13). Comparison of the in-situ sensing results using 1 with the CD signature of 4 obtained under typical assay conditions gave superimposable spectra, which confirms the proposed reaction outcome. Accordingly, the addition of more than two equivalents of 1 to a solution containing cysteine does not further change the chiroptical readout and substantially diminished Cotton effects were observed when only one sensor equivalent was employed in the assay protocol. The cysteine sensing also results in the appearance of a new UV absorption band at approximately 350 nm (see, e.g., FIG. 2A (left)). The off-on UV response occurs almost immediately upon mixing and reaches a stable maximum within a few minutes (FIGS. 24A-B). As mentioned above, a nonenantioselective UV readout bears the chance to determine total D/L-cysteine levels, which would complement the ee analysis based on the induced CD effects.

Figure 2B:
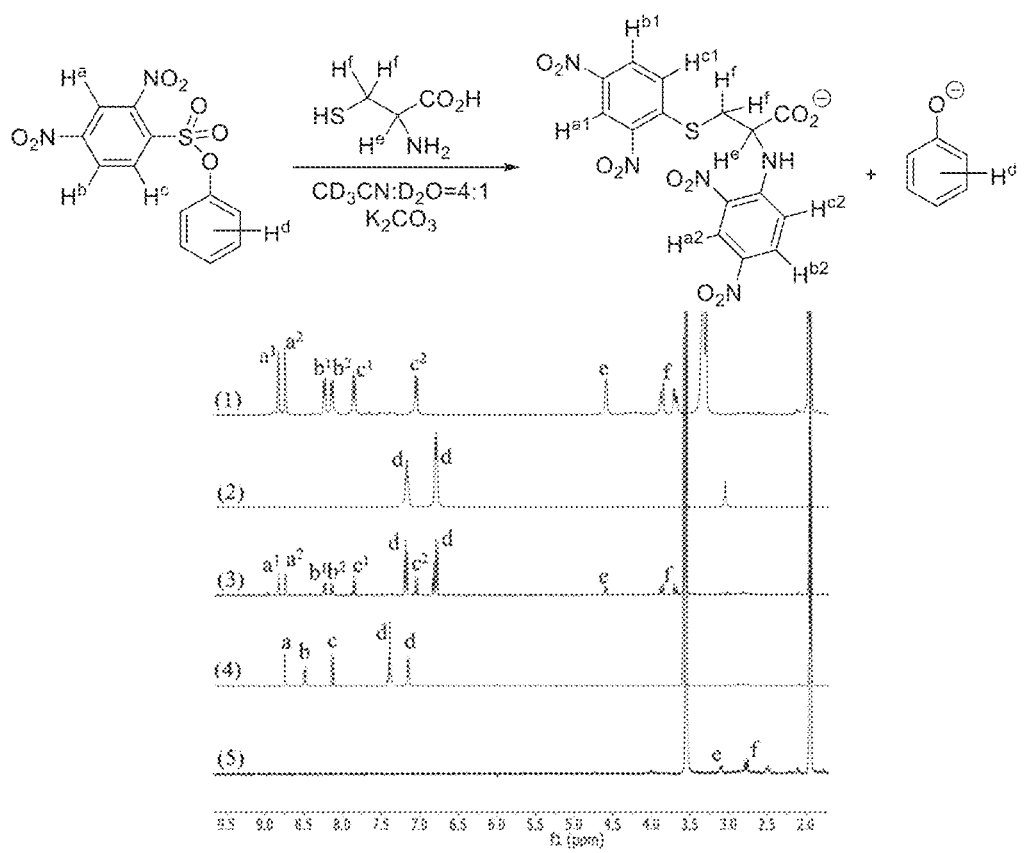
Figure 2C:
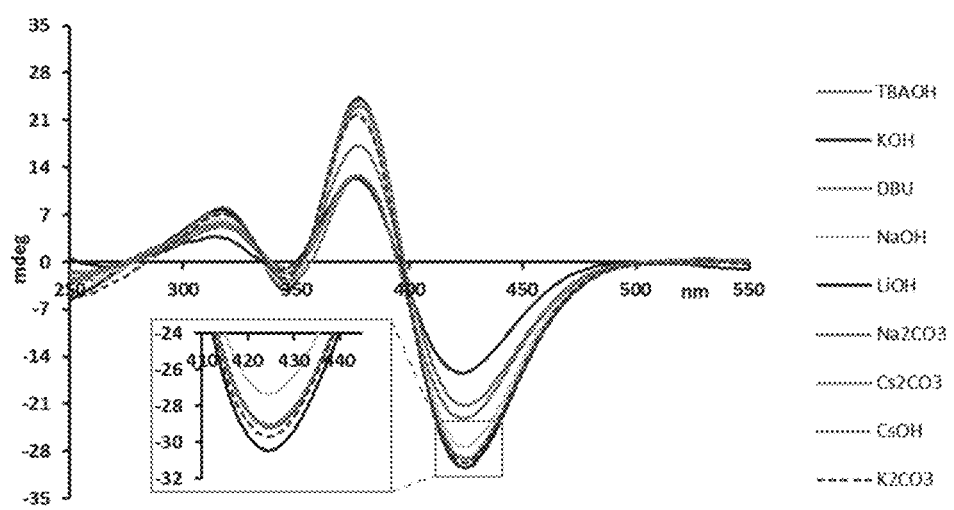

In addition, the sensing reaction was monitored by NMR spectroscopy using essentially the same conditions as applied in the chiroptical sensing experiments (FIG. 2B). Quantitative conversion of free cysteine to the N,S-diarylation product 4 and simultaneous generation of free phenolate occurred within 7 minutes. The reaction is apparently fast and no by-products were detected, which is an important prerequisite for quantitative sensing analysis. Comparison of the NMR spectra obtained with the sensing mixture with the independently prepared compound 4 and phenol in deuterated acetonitrile:water containing four equivalents of K$_2$CO$_3$ allowed unequivocal reaction analysis (FIG. 2B). The attachment of the electron-deficient 3,5-dinitrophenyl rings to the amino and thiol groups results in very strong downfield shifts of the aliphatic cysteine protons H$^e$ and H$^f$. For example, the proton H$^e$ attached to the chiral carbon center shifted from 3.26 to 4.59 ppm. The ipso-substitutions generate two distinguishable 3,5-dinitrophenyl rings. Attachment to the amino moiety causes distinct upfield-shifting of H$^b$ and H$^c$ from 8.49 and 8.13 ppm to 8.14 and 7.05 ppm (labeled as H$^{b2}$ and H$^{c2}$). As expected, the changes in the NMR shifts are less pronounced for H$^{b1}$ and H$^{c1}$ and for the most downfield-shifted proton H$^a$. The concomitant cleavage of phenolate from the probe coincides with an upfield shift of the H$^d$ protons from 7.15 and 7.39 ppm to 7.17 and 6.79 ppm, respectively. Altogether, the UV, CD, and NMR experiments demonstrate that quantitative conversion of Cys toward 4 can be accomplished with stoichiometric sensor amounts and the use of large excess of the probe is not necessary. Further studies revealed that aqueous methanol and acetonitrile solutions are suitable solvent mixtures, albeit the latter generates more intense and slightly red-shifted CD and UV signals (FIGS. 21 and 22). Finally, nine inorganic and organic bases were screened to optimize the sensitivity of the cysteine sensing method. The best results were obtained with NaOH, 1,8-diazabicyclo[5.4.0] undec-7-ene (DBU), KOH, and K$_2$CO$_3$, which was used for all other sensing studies.

Example 6-Cysteine Specificity and Competition Experiments

Experimental Procedures

Generally.

Figure 3A:
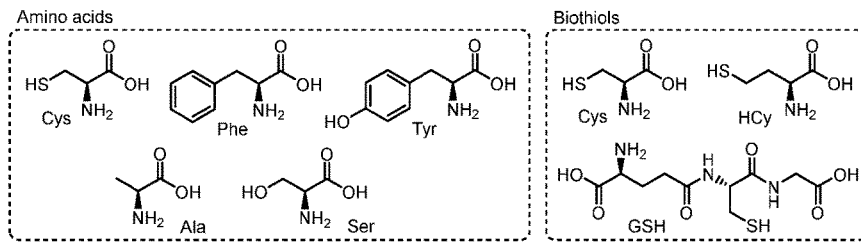
FIGS. 3A-C relate to the determination of cysteine specificity.

Sensing experiments were performed at 1.25 mM cysteine concentration in the presence of other amino acids and competitive biothiols (see FIG. 3A). The CD spectra of the resulting mixtures were collected with a standard sensitivity of 100 mdeg, a data pitch of 0.5 nm, a bandwidth of 1 nm, in a continuous scanning mode with a scanning speed of 500 nm/min and a response of 1 s, using a quartz cuvette (1 cm path length). The data were baseline corrected and smoothed using a binomial equation. UV spectra were collected with an average scanning time of 0.0125 s, a data interval of 5.00 nm, and a scan rate of 400 nm/s.

Selectivity of Probe 1 Towards Cysteine in the Presence of Other Amino Acids.

Figure 3B:
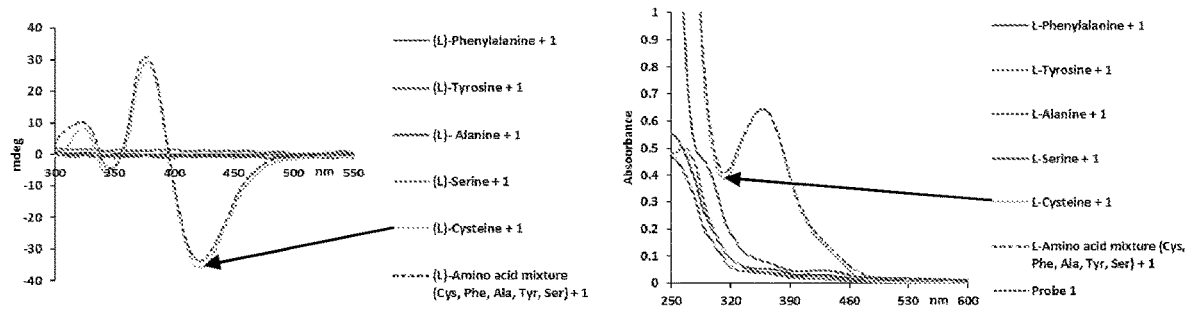

The selectivity of probe 1 towards cysteine in the presence of phenylalanine, alanine, serine, and tyrosine was investigated (FIG. 3B). Solutions of probe 1 (2.50 mM) containing one of the aforementioned L-amino acids (1.25 mM) in the presence of K$_2$CO$_3$ (5 mM) in 3 mL of CH$_3$CN: water (4:1) were stirred for 1 hour. In addition, a solution containing all of the amino acids (1.25 mM) and probe 1 (7.5 mM) in the presence of K$_2$CO$_3$ (12.5 mM) in 3 mL of CH$_3$CN:water (4:1) was stirred for 1 hour. The chiroptical responses were analyzed by CD spectroscopy by diluting 200 μL of each reaction mixture to 2.20 mL (110 μM) with CH$_3$CN (FIG. 3B (left)). For UV analysis 45 μL aliquots of each reaction mixture were diluted to 2.045 mL (30 μM) using CH$_3$CN (FIG. 3B (right)).

This assay selectively targets cysteine. No CD response was observed with phenylalanine, tyrosine, alanine, and serine. The presence of these amino acids did not alter the chiroptical sensor response to cysteine. Identical Cotton effects were obtained with L-cysteine and with a solution containing L-cysteine in the presence of all other amino acids. (FIG. 3B (left)).

No significant UV response was obtained with phenylalanine, tyrosine, alanine, and serine at 355 nm. The presence of these amino acids did not alter the optical sensor response to cysteine. Identical UV maxima at 355 nm were obtained with L-cysteine and with a solution containing L-cysteine in the presence of all other amino acids. (FIG. 3B (right)).

Selectivity of Probe 1 Towards Cysteine in the Presence of Other Biothiols.

Figure 3C:
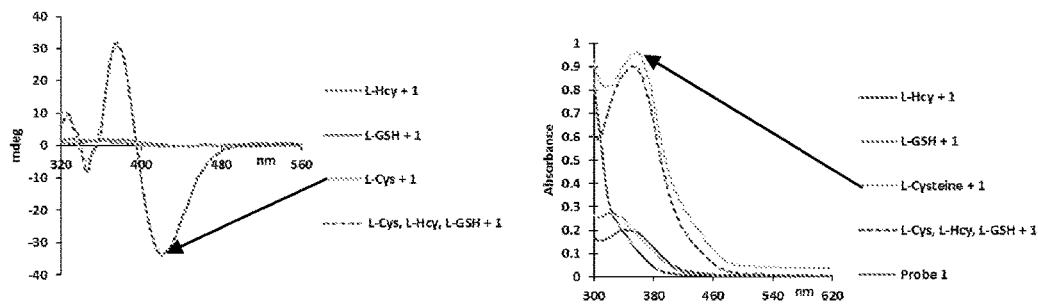

The selectivity of probe 1 towards cysteine in the presence of homocysteine and glutathione was investigated (FIG. 3C). Solutions of 1 (2.5 mM) containing one of the L-biothiols (1.25 mM) in the presence of K$_2$CO$_3$ (5 mM) in 3 mL of CH$_3$CN:water (4:1) was stirred for 1 hour. In addition, a solution containing L-cysteine, L-homocysteine, and L-glutathione (1.25 mM) was treated with probe 1 (7.5 mM) in the presence of K$_2$CO$_3$ (12.5 mM) in 3 mL of CH$_3$CN:water (4:1) for 1 hour. The chiroptical responses were analyzed by CD spectroscopy by diluting 200 μL of each reaction mixture to 2.20 mL (110 μM) with CH$_3$CN (FIG. 3C (left)). For UV analysis aliquots of 45 μL of each reaction mixture were diluted to 2.045 mL (30 μM) using CH$_3$CN (FIG. 3C (right)).

This assay selectively targets cysteine. No CD response was observed with homocysteine and glutathione. The presence of these biothiols did not alter the chiroptical sensor response to cysteine. Identical Cotton effects were obtained with L-cysteine and with a solution containing L-cysteine in the presence of L-homocysteine and L-glutathione. (FIG. 3C (left)).

The presence of homocysteine and glutathione did not alter the optical sensor response to cysteine significantly. Identical UV maxima at 355 nm were obtained with L-cysteine and with a solution containing L-cysteine in the presence of L-homocysteine and L-glutathione. (FIG. 3C (right)).

Results and Discussion

The irreversibility of the N,S-diarylation reaction and the hydrolytic stability of both the probe and N,S-bis(2,4-dinitrophenyl)cysteine allow smooth and unambiguous Cys derivatization devoid of interfering by-product formation. The conversion to the chiroptically active product 4 coincides with characteristic and stable UV and CD signals at high wavelengths. Having thus established the basic prerequisites for quantitative stereochemical cysteine sensing, the possibility of substrate specificity in the presence of other substances was evaluated. Interfering stoichiometric amounts of amino acids were tested with phenylalanine, alanine, serine, and tyrosine as representative examples. First, solutions containing probe 1 (2.50 mM) and one of the aforementioned L-amino acids or L-Cys (1.25 mM) in the presence of $K_2CO_3$ (5 mM) in 3 mL of $CH_3CN$:water (4:1) were stirred for 1 hour. The mixtures were then further diluted for CD and UV analysis (FIG. 3B). All mixtures remained CD silent with the exception of the cysteine solution and similar results were obtained by UV analysis. A solution containing the five amino acids altogether with six equivalents of 1 under otherwise the same conditions was prepared to determine possible interference with the cysteine sensing. Importantly, essentially identical CD and UV responses were measured, which highlights a remarkable specificity of this assay for cysteine.

Figure 31:
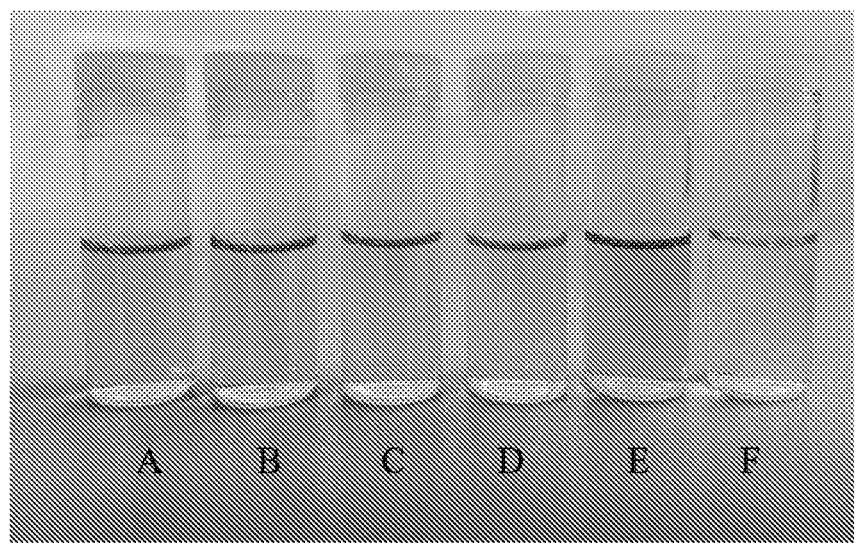
FIG. 31 is a picture of various solutions showing the naked eye detection of cysteine at 1.25 mM. A: L-Serine+probe 1; B: L-Phenyl Alanine+probe 1; C: L-Alanine+probe 1; D: L-Tyrosine+probe 1; E: L-Cysteine+probe 1; F: Probe 1.

The screening of L-homocysteine and L-glutathione, which are common biothiols that often impede the selective targeting of cysteine, was next tested. Glutathione, a cysteine-derived tripeptide, and the non-proteinogenic amino acid homocysteine, which differs only by one additional methylene group from cysteine, display free amine and thiol groups and are therefore very difficult to distinguish from cysteine. When the sensing assay with probe 1 was applied to these biothiols under the conditions described above for the amino acid analysis, a relatively weak UV response was observed in the 300 nm region but no induction of a CD signal, which is in stark contrast to the cysteine sensing results (FIG. 3C). Furthermore, the analysis of a mixture consisting of Cys, HCy, and GSH revealed only a minor contribution of these two biothiols to the UV readout while the CD sensing was not affected at all. The induced Cotton effects obtained with samples containing either L-Cys or a combination of L-Cys, L-HCy, and L-GSH at individual 1.25 mM concentrations in aqueous acetonitrile were virtually identical. The competition experiments thus prove a remarkable specificity of the chiroptical sensing method for cysteine over other amino acids and common biothiols. The optical detection mode is also visible to the naked eye and allows colorimetric cysteine analysis in the presence of amino acids and biothiols (FIG. 31).

Example 7-Quantitative Cysteine Analysis at µM Concentrations

Quantitative Cysteine Sensing: Absolute Configuration, Enantiomeric Excess and Total Concentration Generally.

The CD spectra of sensing mixtures were collected with a standard sensitivity of 100 mdeg, a data pitch of 0.5 nm, a bandwidth of 1 nm, in a continuous scanning mode with a scanning speed of 500 nm/min and a response of 1 s, using a quartz cuvette (1 cm path length). The data were baseline corrected and smoothed using a binomial equation. UV spectra were collected with an average scanning time of 0.0125 s, a data interval of 5.00 nm, and a scan rate of 400 nm/s.

Determination of the Concentration of Cysteine Using Probe 1.

Figure 32A:
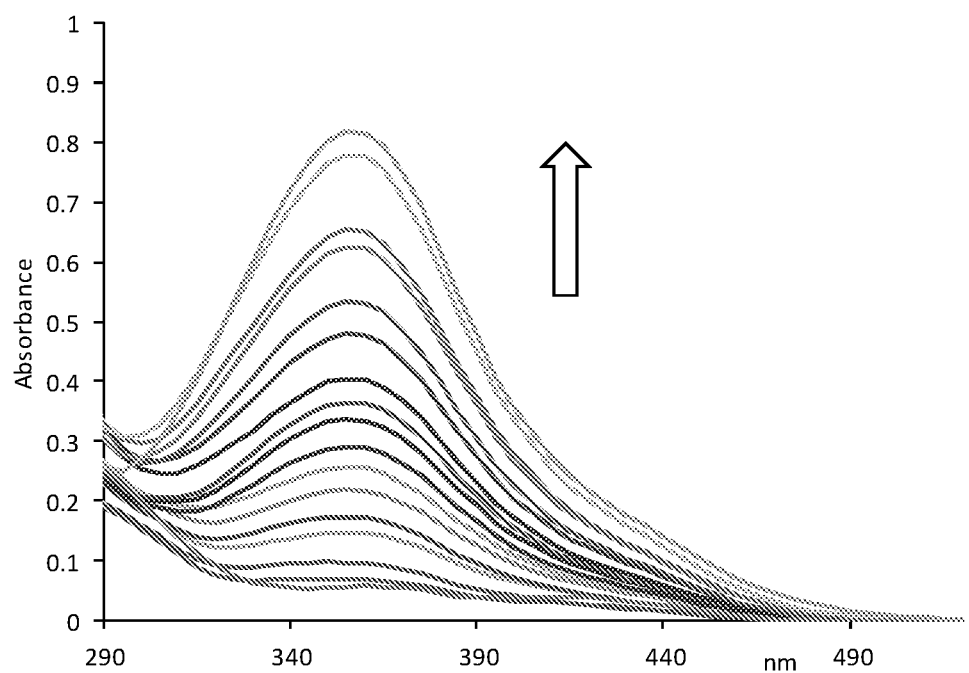
FIGS. 32A-B are the UV spectra (FIG. 32A) obtained from the reaction between probe 1 and varying amounts of L-cysteine and a plot (FIG. 32B) of the UV absorbance at 355 nm versus the concentration of L-cysteine. The absorbance values are proportional to the cysteine concentrations tested.
Figure 32B:
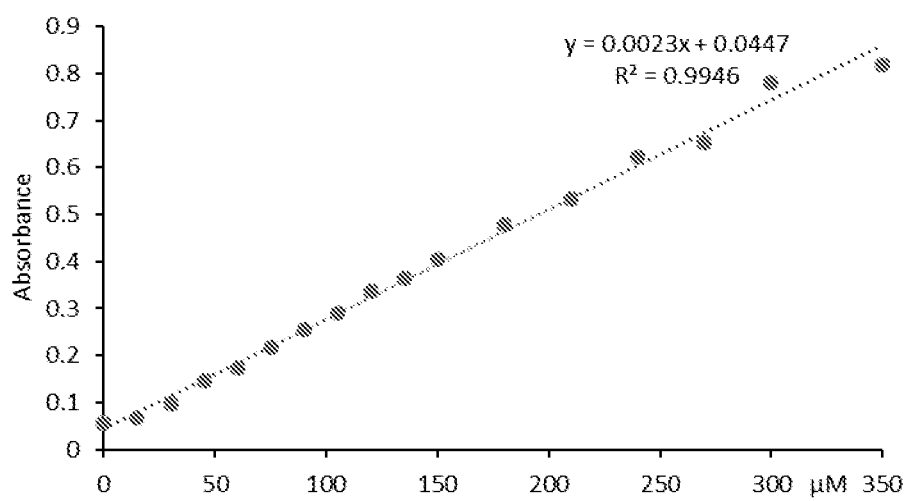

The change in the UV absorbance of probe 1 upon cysteine sensing was analyzed (FIGS. 32A-B). Probe 1 (750 µM) and L-cysteine in varying concentrations (0, 15, 30, 45, 60, 75, 90, 105, 120, 135, 150, 180, 210, 240, 270, 300, and 350 µM) were dissolved in the presence of $K_2CO_3$ (1.44 mM) in 2.5 mL of $CH_3CN$:water (4:1). To 250 µL of this solution, acetonitrile (2 mL) was added and the mixture was subjected to UV analysis (FIG. 32A). The UV absorbance at 355 nm increased as the concentration of cysteine changed from 0 to 350 µM. Plotting and curve fitting of the UV absorbance at 355 nm against the concentration (µM) of cysteine gave a linear equation (y=0.0023x+0.0447) with $R^2$=0.9946 (FIG. 32B).

Determination of the Enantiomeric Excess of Cysteine Using Probe 1.

Figure 33A:
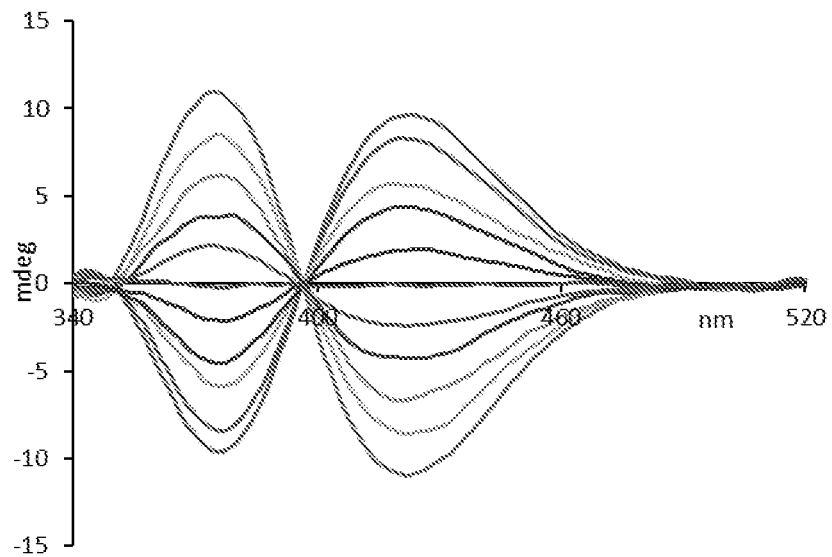
FIGS. 33A-B are the CD spectra (FIG. 33A) showing the chiroptical response of probe 1 to scalemic samples of L-cysteine and a plot (FIG. 33B) of the CD amplitudes at 375 nm (lower left and upper right quadrants) and 422 nm (upper left and lower right quadrants) versus sample ee. The peak amplitudes are proportional to the enantiomeric excess of the sample.
Figure 33B:
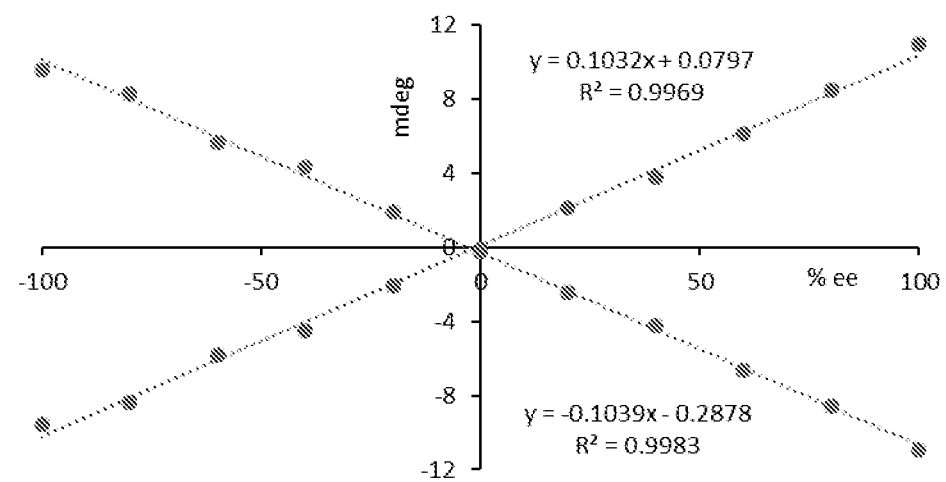

A calibration curve was constructed using samples containing cysteine with varying enantiomeric composition. Probe 1 (750 µM) and L-cysteine (50 µM) with varying ee's (+100, +80, +60, +40, +20, 0, −20, −40, −60, −80, −100% ee) were dissolved in the presence of $K_2CO_3$ (1.44 mM) in 2.5 mL of $CH_3CN$:water (4:1). After 1.5 hours, CD analysis was carried out using 2 mL of the mixture without further dilution (50 µM) (FIG. 33A). The CD amplitudes at 375 and 422 nm were plotted against the enantiomeric excess of cysteine (FIG. 33B).

Linearity of the CD Response Versus the Concentration of Cysteine.

Figure 4A:
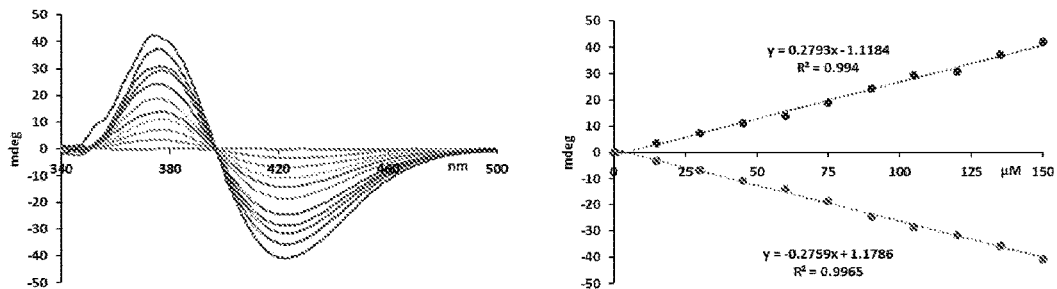
FIGS. 4A-B relate to quantitative cysteine recognition.

The change in the CD response of probe 1 upon cysteine recognition was analyzed using varying concentrations of enantiopure L-cysteine (FIG. 4A). Probe 1 (750 µM) and L-cysteine in varying concentrations (0, 15, 30, 45, 60, 75, 90, 105, 120, 135, 150, 180, 210, 240, 270, 300, and 350 µM) were dissolved in the presence of $K_2CO_3$ (1.44 mM) in 2.5 mL of $CH_3CN$:water (4:1). After 1.5 hours, CD analysis was carried out using 2 mL of the mixture without further dilution (FIG. 4A (left)). Plotting of the CD amplitudes at 376 and 423 nm of the corresponding reaction mixture against the amount of cysteine showed a linear chiroptical response (FIG. 4A (right)).

Simultaneous ee and Concentration Determination.

Six scalemic samples of cysteine were prepared and subjected to simultaneous analysis of the concentration, ee, and absolute configuration using probe 1. First, a UV spectrum was obtained as described above and the concentration was calculated using regression equation (1) below. Then, a CD spectrum was obtained as described above. This value was then applied in the linear regression equations (2) and (3) to determine the enantiomeric excess. The absolute configuration was determined using the sign of the Cotton effect. The results are shown in Table 1 below.

$$x = \frac{(y - 0.0447)}{0.0023} \quad \text{(Equation 1; x in μM)}$$

At 375 nm;

$$ee = \frac{\left(\frac{(mdeg \times 50)}{x} - 0.0797\right)}{0.1032} \quad \text{(Equation 2)}$$

At 422 nm;

$$ee = \frac{\left(\frac{(mdeg \times 50)}{x} + 0.2878\right)}{(-0.1039)} \quad \text{(Equation 3)}$$

TABLE 1

Concentration, ee, and absolute configuration of samples of cysteine determined by the combined UV and CD responses of probe 1.

| Cysteine samples | | | Sensing results | | | | |
|---|---|---|---|---|---|---|---|
| Abs. config. | Concentration (μM) | % ee | Abs. config. | Concentration (μM) | % ee (375 nm) | % ee (422 nm) | Average % ee |
| D | 100 | −40.0 | D | 105.5 | −41.3 | −46.8 | −44.1 |
| L | 50 | +80.0 | L | 54.8 | +86.1 | +80.6 | +83.4 |
| L | 75 | +20.0 | L | 79.5 | +26.5 | +23.9 | +25.2 |
| D | 90 | −11.1 | D | 95.4 | −10.5 | −15.0 | −12.8 |
| L | 18 | +44.4 | L | 21.0 | +43.4 | +38.8 | +41.1 |
| L | 40 | +25.0 | L | 42.0 | +29.0 | +26.0 | +27.5 |

Sensing of Cysteine at Micromolar Concentrations.

A concentration range of 15-30 μM of cysteine has been reported in healthy adult humans and elevated levels of cysteine in the body have been used as indicator for increased risk of Alzheimer's and heart disease. (Oyane et al., *J. Biomed. Mater. Res. A.* 65:188-195 (2003); Brigham et al., 39:1633-1638 (1960), each of which is hereby incorporated by reference in its entirety.) The possibility of cysteine sensing at these physiologically relevant levels was investigated.

Figure 34:
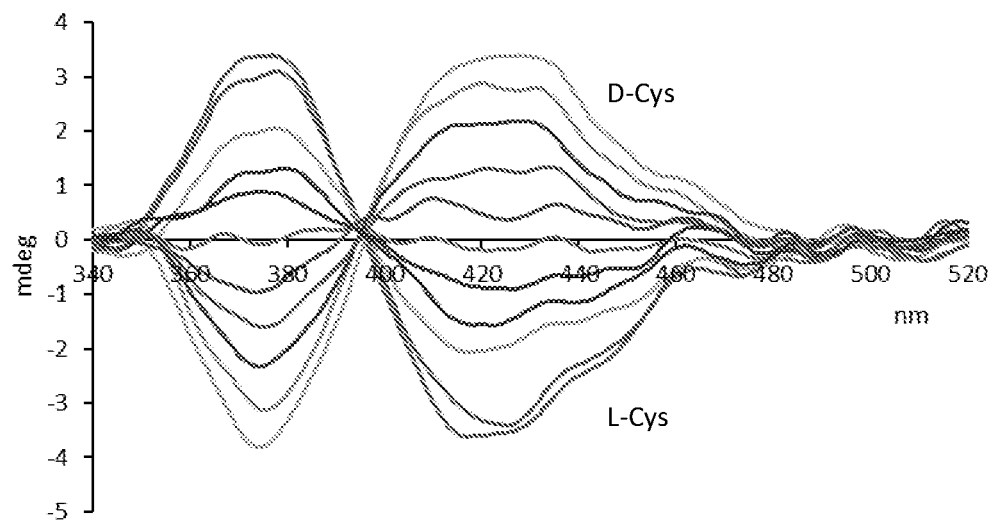
FIG. 34 is the CD spectra showing the chiroptical response of probe 1 to scalemic samples of cysteine at 15 μM. The peak amplitudes are proportional to the enantiomeric excess of the sample. (See also FIG. 4B.)

Probe 1 (150 μM) and L-cysteine (15 μM) with varying ee's (+100, +80, +60, +40, +20, 0, −20, −40, −60, −80, −100% ee) were dissolved in the presence of $K_2CO_3$ (60 μM) in 2.5 mL of $CH_3CN$:water (4:1). After 1.5 hours, CD analysis was carried out using 2 mL of the mixture without further dilution (15 μM) (FIG. 4B (left) and FIG. 34). The CD amplitudes at 377 and 417 nm were plotted against the enantiomeric excess of cysteine (FIG. 4B (right)). The results show that quantitative analysis of micromolar cysteine concentrations is possible.

Results and Discussion

Figure 4B:
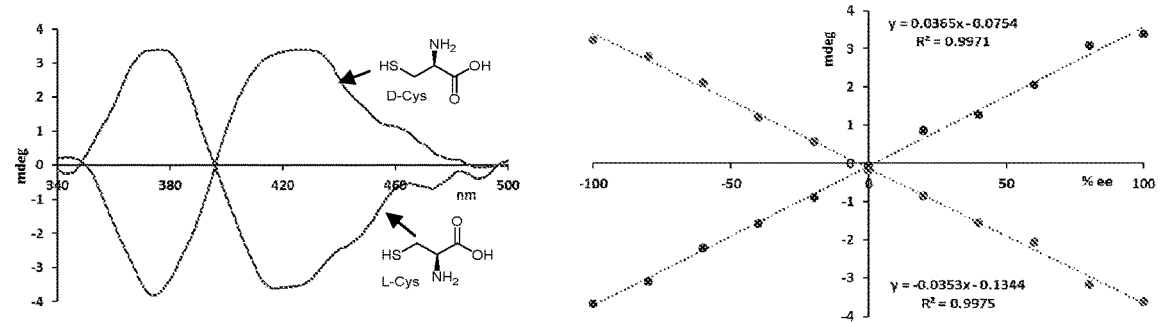

Further CD analysis revealed that the chiroptical sensor response increases linearly with the enantiomeric excess and also with the concentration of cysteine (FIG. 4A). In addition, the sensing is rugged and practical as recalibration of the UV and CD responses of the probe is not necessary. Having once established the quantitative correlations between the induced UV and CD signals to the concentration and ee of cysteine, the possibility of sensing at physiologically relevant levels was tested. A concentration range of 15-30 μM of cysteine in healthy adults has been reported and elevated levels of cysteine in the human body have been used as indicator for increased risk of Alzheimer's and heart disease. (Oyane et al., *J Biomed. Mater. Res. A.* 65:188-195 (2003); Brigham et al., 39:1633-1638 (1960), each of which is hereby incorporated by reference in its entirety.) The possibility of chiroptical cysteine sensing at these concentrations was investigated. Initial CD sensing tests indicated that nonracemic mixtures at 15 μM generate sufficient Cotton effects and can easily be detected and quantified (FIG. 4B). This encouraged the ultimate testing of the assay and the probe was applied to six nonracemic samples combining a wide range of cysteine amounts and enantiomeric ratios (Table 2).

TABLE 2

Comprehensive chirality sensing of nonracemic cysteine samples.

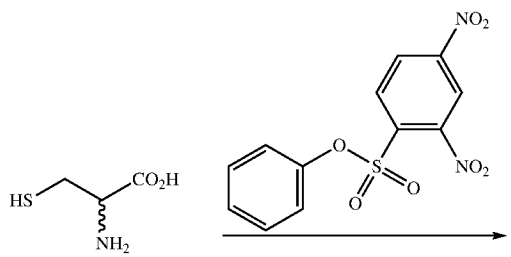

total concentration?
absolute configuration?
enantiomeric D/L ratio?

TABLE 2-continued

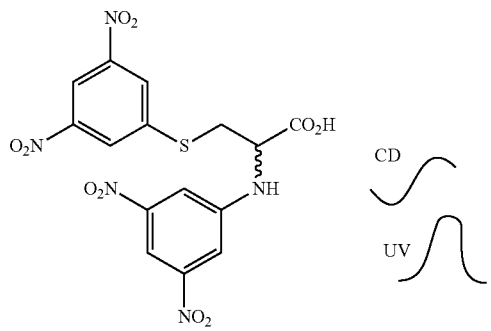

| | Cysteine Samples | | | Chiroptical Sensing Results | | | | |
|---|---|---|---|---|---|---|---|---|
| Entry | Abs. Config.[a] | Conc. (μM) | D/L Ratio | Abs. Config.[a] | Conc. (μM) | D/L Ratio (375 nm) | D/L Ratio (422 nm) | Average[b] D/L Ratio |
| 1 | D | 100 | 70.0:30.0 | D | 105.5 | 70.6:29.4 | 73.4:26.6 | 72.1:27.9 |
| 2 | L | 50 | 10.0:90.0 | L | 54.8 | 6.9:93.1 | 9.7:90.3 | 8.3:91.7 |
| 3 | L | 75 | 40.0:60.0 | L | 79.5 | 36.6:63.4 | 38.1:61.9 | 37.4:62.6 |
| 4 | D | 90 | 55.5:44.5 | D | 95.4 | 55.2:44.8 | 57.5:42.5 | 56.4:43.6 |
| 5 | L | 18 | 27.8:72.2 | L | 21.0 | 28.3:71.7 | 30.6:69.4 | 29.4:70.6 |
| 6 | L | 40 | 37.5:62.5 | L | 42.0 | 35.5:64.5 | 37.0:63.0 | 36.3:63.7 |

[a]Major enantiomer.
[b]Based on the CD sensing at 375 and 422 nm.

Following the simple mix-and-measure protocol described above, two fast UV and CD measurements allowed simultaneous determination of the absolute configuration of the major cysteine isomer (based on the sign of the induced Cotton effect), the enantiomeric ratio (using the induced CD amplitude), and the overall concentration of the combined enantiomers (from the UV response of the probe) with good accuracy and without the need to generate a new calibration curve. Of particular interest is the analysis of the 18 μM sample containing the D-form in 27.8% and the L-enantiomer in 72.2% (Table 2, entry 5). Even at this low concentration the sensing results deviated only by a few percent from the actual values. The assay correctly identified L-cysteine as the major enantiomer and the quantitative concentration and er determination gave 21 μM and an enantiomeric ratio of 29.4:70.6, respectively. Importantly, samples covering a wide concentration range and drastically different enantiomeric ratios can be analyzed by this method (Table 2, compare entry 1 with entry 5 and entry 2 with entry 4).

Example 8-Simulated Body Fluids

Determination of the Concentration, Enantiomeric Excess, and Absolute Configuration of Cysteine in r-SBF (Revised Simulated Body Fluids)

Generally.

A simulated body fluid (SBF) mimics the ion concentration of the human blood plasma. SBFs have been used for in-vitro studies of biologically active compounds. Conventional SBFs have an ion concentration equal to those in the blood plasma, except for $Cl^-$ and $HCO_3^-$. Revised-SBF (r-SBF) have been introduced to eliminate this discrepancy and were used in this Example. (Fuchs et al., *Mol. Genet. Metab.* 85:168-180 (2005), which is hereby incorporated by reference in its entirety.) The concentration and enantiomeric excess of cysteine at micromolar concentrations in r-SBF were determined using probe 1.

Concentration Analysis of Cysteine Samples Using Probe 1.

Figure 35A:
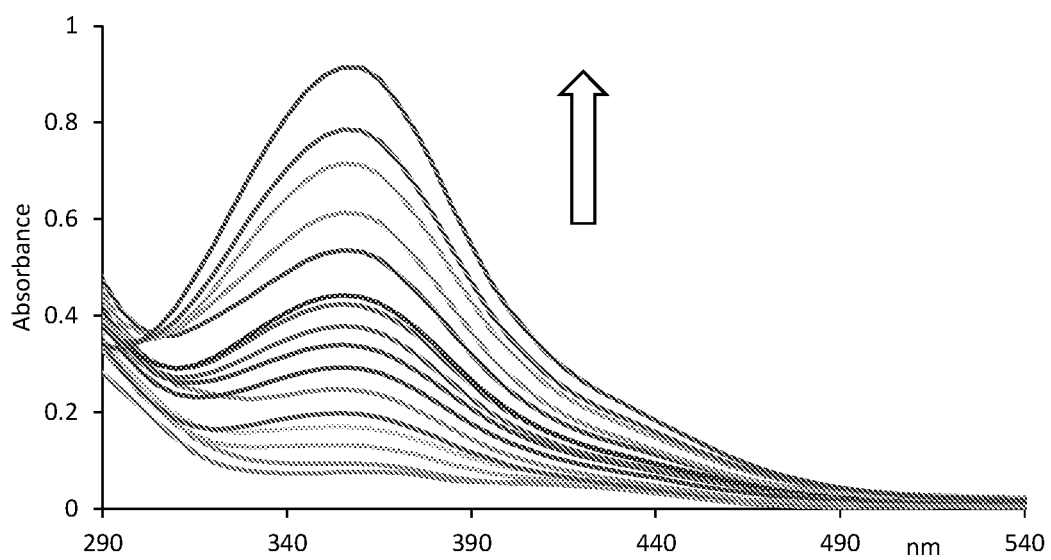
FIGS. 35A-B are the UV spectra (FIG. 35A) obtained from the reaction between probe 1 and varying concentrations of L-cysteine and a plot (FIG. 35B) of the UV absorbance measured at 355 nm versus the concentration of L-cysteine. The absorbance values are proportional to the cysteine concentrations tested.
Figure 35B:
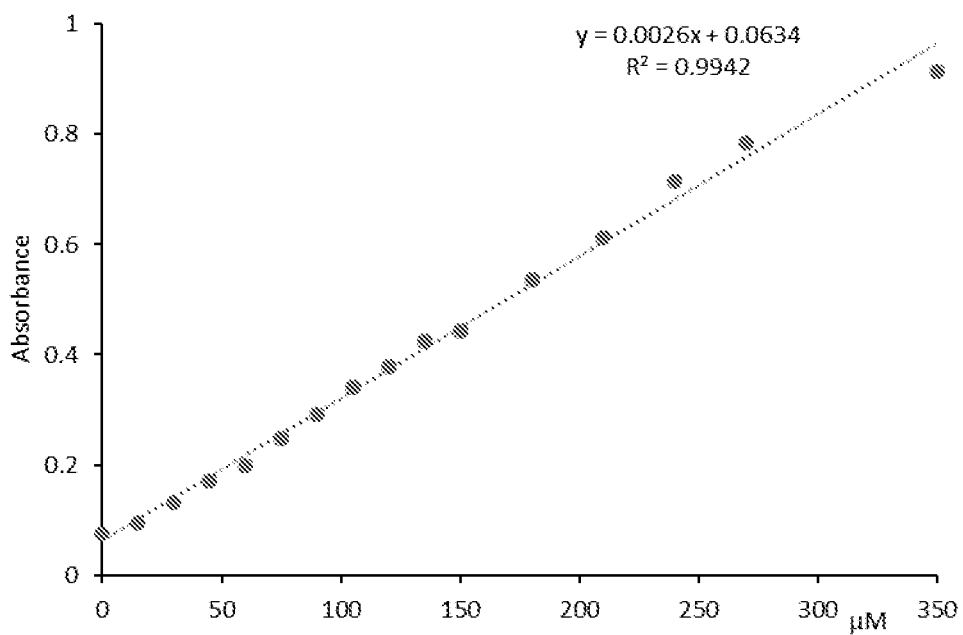

The change in the UV absorbance of probe 1 upon cysteine sensing was analyzed (FIGS. 35A-B). A calibration curve was constructed with samples containing various amounts of cysteine in r-SBF. Probe 1 (750 μM) and L-cysteine in r-SBF in varying concentrations (0, 15, 30, 45, 60, 75, 90, 105, 120, 135, 150, 180, 210, 240, 270, 300, and 350 μM) were dissolved in the presence of $K_2CO_3$ (1.44 mM) in 2.5 mL of $CH_3CN$:water (4:1). To 250 μL of this solution, acetonitrile (2 mL) was added and the mixture was subjected to UV analysis (FIG. 35A). The UV absorbance at 355 nm increased linearly as the concentration of cysteine changed from 0 to 350 μM. Plotting and curve fitting of the UV absorbance at 355 nm against the concentration (μM) of cysteine gave a linear equation (y=0.0026x+0.0634) with $R^2$=0.9942 (FIG. 35B).

Enantiomeric Excess Analysis of Cysteine Samples Using Probe 1.

Figure 36A:
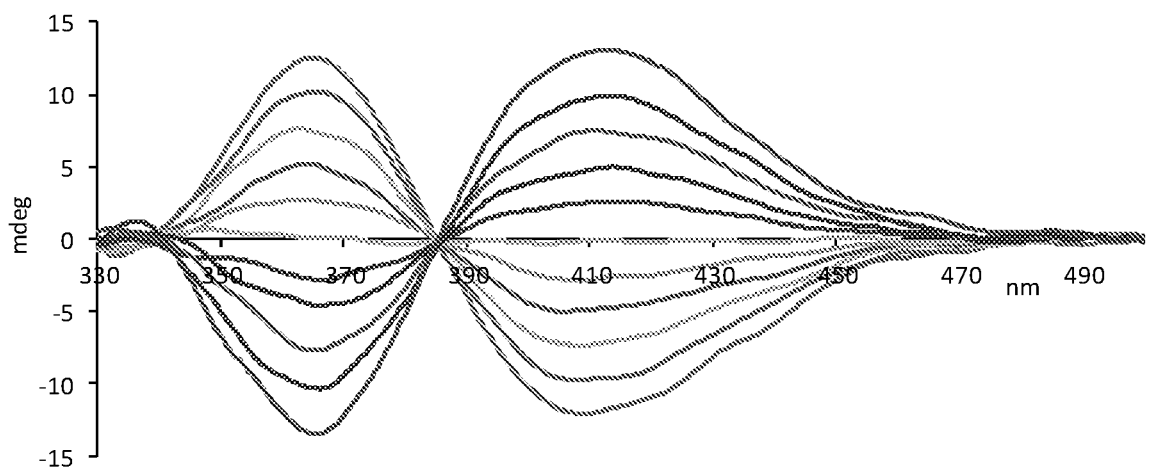
FIGS. 36A-B are the CD spectra (FIG. 36A) showing the chiroptical response of probe 1 to scalemic samples of cysteine and a plot (FIG. 36B) of the chiroptical response at 365.5 nm (lower left and upper right quadrants) and 409 nm (upper left and lower right quadrants) versus cysteine ee. The peak amplitudes are proportional to the enantiomeric excess of the sample.
Figure 36B:
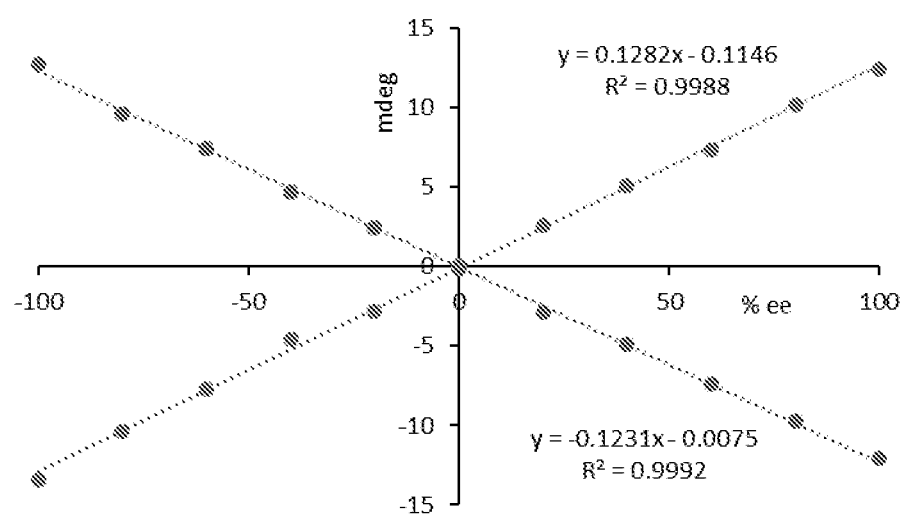

A calibration curve was constructed using samples containing cysteine in r-SBF with varying enantiomeric composition. Probe 1 (750 μM) and L-cysteine (50 μM) with varying ee (+100, +80, +60, +40, +20, 0, −20, −40, −60, −80, −100% ee) were dissolved in the presence of $K_2CO_3$ (1.44 mM) in 2.5 mL of $CH_3CN$:water (4:1). After 1.5 hours, CD analysis was carried out using 2 mL of the mixture without further dilution (50 μM) (FIG. 36A). The CD amplitudes at 365.5 and 409 nm were plotted against the enantiomeric excess of cysteine (FIG. 36B).

Simultaneous ee and Concentration Determination.

Six scalemic samples of cysteine were prepared and subjected to simultaneous analysis of the concentration, ee, and absolute configuration using probe 1. First, a UV spectrum was obtained as described above, and the concentration was calculated using the regression equation (1) below. Then, a CD spectrum was obtained as described above. This value was then applied in the linear regression equations (2) and (3) to determine the enantiomeric excess.

The absolute configuration was determined using the sign of the induced Cotton effect. The results are shown in Table 3 below.

$$x = \frac{(y - 0.0634)}{0.0026} \quad \text{(Equation 1; x in μM)}$$

At 365.5 nm;

$$ee = \frac{\left(\frac{(mdeg \times 50)}{x} + 0.1146\right)}{0.1282} \quad \text{(Equation 2)}$$

At 409 nm;

$$ee = \frac{\left(\frac{(mdeg \times 50)}{x} + 0.0075\right)}{(-0.1231)} \quad \text{(Equation 3)}$$

TABLE 3

Concentration, ee, and absolute configuration of samples of cysteine determined by the combined UV and CD responses of probe 1.

| Cysteine samples | | | Sensing results | | | | |
|---|---|---|---|---|---|---|---|
| Abs. config. | Concentration (μM) | % ee | Abs. config. | Concentration (μM) | % ee (365.5 nm) | % ee (409 nm) | Average % ee |
| L | 130 | +53.8 | L | 129.0 | +52.2 | +51.0 | +51.6 |
| D | 90 | −11.1 | D | 89.6 | −11.0 | −10.6 | −10.8 |
| L | 75 | +20.0 | L | 73.1 | +17.0 | +19.0 | +18.0 |
| D | 100 | −40.0 | D | 102.9 | −38.0 | −39.1 | −38.6 |
| L | 15 | +33.3 | L | 16.6 | +23.0 | +28.2 | +25.6 |
| L | 40 | +50.0 | L | 35.1 | +44.0 | +42.9 | +43.5 |

Results and Discussion

Because brain fluids and other biological samples containing amino acids in varying nonracemic compositions are not generally available, simulated body fluids (SBFs) were used. SBFs mimic the human blood plasma and have been used for in-vitro studies of biologically active compounds. Conventional SBFs have ion concentrations equal to typical values in blood plasma, except for chloride and bicarbonate. A revised-SBF (r-SBF) composition has been introduced to eliminate this discrepancy and was selected to test the ruggedness and usefulness of the Cys sensing assay. (Salemi et al., *Neurol. Sci.* 30:361-364 (2009), which is hereby incorporated by reference in its entirety.) The concentration and enantiomeric ratio of cysteine at micromolar concentrations in r-SBFs containing ions at physiologically relevant levels were determined using probe 1 as described above. The r-SBF was prepared from NaCl, NaHCO$_3$, Na$_2$CO$_3$, KCl, K$_2$HPO$_4$, MgCl$_2$, HEPES, CaCl$_2$, Na$_2$SO$_4$, and by using 1M NaOH and HCl to adjust the pH to 7.40 as described in detail in the literature. The results obtained with six nonracemic samples are shown in Table 4. Again, the absolute configuration of the major isomer together with the ratio and the total concentration of the cysteine enantiomers were determined correctly and with good accuracy. For example, analysis of the sample containing cysteine at 130 μM with an enantiomeric D/L ratio of 23.1:76.9 gave 129 μM and 24.2:75.8, respectively (Table 4, entry 1). A comparison of the actual with the experimentally determined data obtained for the second sample (90 μM, D/L 55.5:44.5) shows almost identical values (89.6 μM, D/L 55.4:44.6). Overall, significant interference with the cysteine sensing in simulated body fluids is not observed and the sensitivity of this method is not compromised as is evident from the analysis of a 15 μM sample with a D/L ratio of 33.3:66.7. In this case, the concentration was determined as 16.6 μM and the enantiomeric ratio as 37.2:62.8 (Table 4, entry 5).

TABLE 4

Analysis of nonracemic cysteine samples in simulated body fluids.

| | Cysteine Samples | | | Chiroptical Sensing Results | | |
|---|---|---|---|---|---|---|
| Entry | Abs. Config.[a] | Conc. (μM) | D/L Ratio | Abs. Config.[a] | Conc. (μM) | D/L Ratio[b] |
| 1 | L | 130 | 23.1:76.9 | L | 129.0 | 24.2:75.8 |
| 2 | D | 90 | 55.5:44.5 | D | 89.6 | 55.4:44.6 |
| 3 | L | 75 | 40.0:60.0 | L | 73.1 | 41.0:59.0 |
| 4 | D | 100 | 70.0:30.0 | D | 102.9 | 69.3:30.7 |
| 5 | L | 15 | 33.3:66.7 | L | 16.6 | 37.2:62.8 |
| 6 | L | 40 | 25.0:75.0 | L | 35.1 | 28.2:71.8 |

[a]Major enantiomer.
[b]Averaged value based on the CD sensing at 366 and 409 nm.

Discussion of Examples 1-8

Three small-molecule probes were synthesized that are stable to hydrolysis and carry a transferable dinitroaryl moiety for substrate-specific optical sensing of cysteine. The chromophoric probes used in Examples 1-8 attach to the thiol and amino functions of the targeted cysteine within minutes in aqueous solution. The reaction course and outcome with one of the probes was verified by NMR spectroscopy, and by comparison of the UV and circular dichroism readouts observed upon in situ cysteine sensing with the chiroptical signals of separately prepared and fully characterized N,S-bis(2,4-dinitrophenyl)cysteine. The double ipso-substitution results in strong spectroscopic readouts at high wavelengths which provides detailed information about the absolute configuration, enantiomeric ratio, and total concentration of cysteine. The absolute configuration of the major amino acid enantiomer and the D/L ratio can be readily determined from the sign and amplitude, respectively, of the induced CD signals appearing at approximately 370 and 410 nm. In addition, a new UV absorption band at approximately 350 nm appears that is independent of the enantiomeric sample composition and correlated to the overall cysteine concentration. The molecular detection and stereochemical sensing of cysteine is highly substrate-specific and the presence of other amino acids (phenylalanine, alanine, serine, and tyrosine were used as representative examples) or biothiols (homocysteine and glutathione) does not interfere with the (chir)optical responses. Finally, quantitative analysis of cysteine in simulated body fluids was demonstrated. The optical assay relies on a practical mix-and-measure protocol and two fast UV and CD measurements that provide comprehensive stereochemical information about the absolute configuration, D/L ratio, and overall amount of cysteine. Samples covering a wide concentration range and drastically different enantiomeric ratios can be analyzed without the need for cumbersome recalibration experiments by this method and accurate values are obtained with aqueous solutions containing cysteine at biologically relevant micromolar levels.

It is predicted from Examples 1-8 that other small molecule probes that comprise a chromophore of the formula

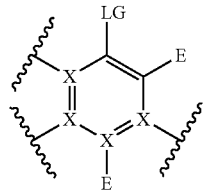

(where X, LG, and E are as defined above), would also be useful for analyzing cysteine. Provided the orientation of the leaving group and electron withdrawing group(s) around the (hetero)arylene ring is conserved, it is expected that the probes can tolerate considerable variation elsewhere.

Although some embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A compound of Formula I:

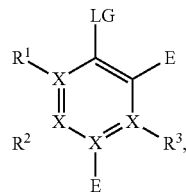

wherein:
each X is independently C or N;
each E is independently hydrogen or an electron withdrawing group selected from the group consisting of —$CF_3$, —C(O)—$R_a$, —$SO_2$—$R_a$, —CN, and —$NO_2$, with the proviso that at least one E is an electron withdrawing group;

LG is a leaving group.

$R^1$ and $R^2$, together with the carbon or nitrogen atoms to which they are attached, form a cycloalkyl, heterocycloalkyl, aryl, or heteroaryl;

$R^3$ is absent or selected from the group consisting of —$R_a$, -cycloalkyl, -heterocycloalkyl, -aryl, and -heteroaryl; and each $R_a$ is independently selected from the group consisting of —H, -alkyl, —O-alkyl, —N-alkyl, -alkenyl, —O-alkenyl, —N-alkenyl, -alkynyl, —O-alkynyl, —N—alkynyl, -aryl, —O-aryl, —N-aryl, -heteroaryl, —O-heteroaryl, —N-heteroaryl, -cycloalkyl, —O-cycloalkyl, —N-cycloalkyl, -heterocycloalkyl, —O—heterocycloalkyl, and —N-heterocycloalkyl;

wherein the compound of Formula I is not

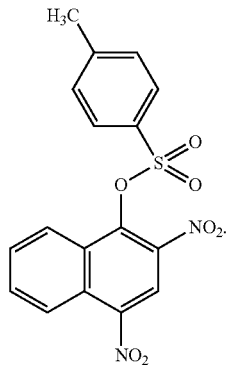 [SMILES: Cc1ccc(S(=O)(=O)Oc2c([N+](=O)[O-])cc([N+](=O)[O-])c3ccccc23)cc1]

2. The compound of claim 1, wherein each X is C.

3. The compound of claim 1, wherein each E is an electron withdrawing group.

4. The compound of claim 3, wherein each E is —$NO_2$.

5. The compound of claim 1, wherein LG is a leaving group selected from the group consisting of halogen, —$OR_b$, —OC(O)$R_b$, —OS(O)$_2R_b$, —S(O)$_2$—O—$R_b$, —$N_2^+$, —$N^+(R_b)_3$, —$S^+(R_b)_2$, and —$P^+(R_b)_3$; wherein each $R_b$ is independently selected from the group consisting of hydrogen, -alkyl, —O-alkyl, —N-alkyl, -alkenyl, —O-alkenyl, —N-alkenyl, -alkynyl, —O-alkynyl, —N-alkynyl, -perfluoroalkyl, -perfluoroalkenyl, -perfluoroalkynyl, -aryl, —O-aryl, —N-aryl, -heteroaryl, —O— heteroaryl, —N-heteroaryl, -cycloalkyl, —O-cycloalkyl, —N-cycloalkyl, -heterocycloalkyl, —O-heterocycloalkyl, and —N-heterocycloalkyl, except that $R_b$ is not p-tolyl when LG is —OS(O)$_2R_b$ and $R_1$ and $R_2$ together form an aryl.

6. The compound of claim 5, wherein the leaving group is

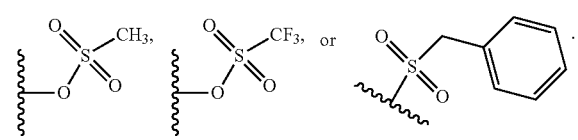 [SMILES: *OS(C)(=O)=O ; *OS(=O)(=O)C(F)(F)F ; *S(=O)(=O)Cc1ccccc1]

7. The compound of claim 6, wherein the leaving group is

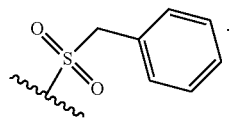 [SMILES: *S(=O)(=O)Cc1ccccc1]

8. The compound of claim 1, wherein $R_1$ and $R_2$, together with the carbon atoms to which they are attached, form a cycloalkyl, aryl, or heteroaryl.

9. The compound of claim 8, wherein $R_1$ and $R_2$, together with the carbon atoms to which they are attached, form a naphthalene ring.

10. The compound of claim 1, where $R^3$ are each hydrogen.

11. The compound of claim 1, wherein the compound is

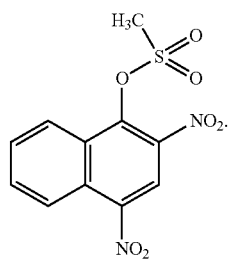 [SMILES: CS(=O)(=O)Oc1c([N+](=O)[O-])cc([N+](=O)[O-])c2ccccc12]

* * * * *